United States Patent
Chakravarthy

(10) Patent No.: US 12,343,532 B1
(45) Date of Patent: Jul. 1, 2025

(54) ARTIFICIAL INTELLIGENCE (AI)-BASED SYSTEM AND METHOD FOR CONTROLLING OPERATIONS OF NEUROMODULATION DEVICES BASED ON PHYSIOLOGICAL PARAMETERS OF USERS

(71) Applicant: NXTSTIM, Inc, San Diego, CA (US)

(72) Inventor: Krishnan Chakravarthy, San Diego, CA (US)

(73) Assignee: NXTSTIM, Inc, San Diego, CA (US)

( * ) Notice: Subject to any disclaimer, the term of this patent is extended or adjusted under 35 U.S.C. 154(b) by 0 days.

(21) Appl. No.: 18/935,853

(22) Filed: Nov. 4, 2024

Related U.S. Application Data

(60) Provisional application No. 63/612,406, filed on Dec. 20, 2023.

(51) Int. Cl.
*A61N 1/36* (2006.01)
*G16H 10/60* (2018.01)
*G16H 20/40* (2018.01)
*A61N 1/04* (2006.01)

(52) U.S. Cl.
CPC ..... *A61N 1/36031* (2017.08); *A61N 1/36034* (2017.08); *G16H 10/60* (2018.01); *G16H 20/40* (2018.01); *A61N 1/0456* (2013.01)

(58) Field of Classification Search
CPC ........... A61N 1/36031; A61N 1/36034; G16H 20/40; G16H 10/60

USPC .......................................................... 607/62
See application file for complete search history.

(56) References Cited

U.S. PATENT DOCUMENTS

2020/0353264 A1* 11/2020 Gillespie ............ A61N 1/36025

* cited by examiner

*Primary Examiner* — Nadia A Mahmood
(74) *Attorney, Agent, or Firm* — Jason C. Cameron

(57) ABSTRACT

An artificial intelligence (AI)-based system and method for controlling operations of neuromodulation devices based on physiological parameters of users is disclosed. The AI-based system comprises one or more physiological parameters sensing endpoint devices and one or more server devices. The one or more physiological parameters sensing endpoint devices are configured to determine the one or more physiological parameters of each user. The one or more server devices comprises a data-obtaining subsystem, a data-processing subsystem, an operational parameter generation subsystem, a data recommendation subsystem, and a plurality of modules. The AI-based system is configured to process the obtained at least one of: the one or more physiological parameters and user-centric data to generate one or more user-centric operational parameters for controlling the operations of the one or more neuromodulation devices. The generation of one or more user-centric operational parameters optimizes neuromodulation therapy based on the user's unique physiologic parameters.

20 Claims, 10 Drawing Sheets

500A

500B

ARTIFICIAL INTELLIGENCE (AI)-BASED SYSTEM AND METHOD FOR CONTROLLING OPERATIONS OF NEUROMODULATION DEVICES BASED ON PHYSIOLOGICAL PARAMETERS OF USERS

TECHNICAL FIELD

Embodiments of the present disclosure relate to medical technology, and more particularly relate to an artificial intelligence (AI)-based system and method for controlling operations of one or more neuromodulation devices based on one or more physiological parameters of one or more users.

BACKGROUND

In an intricate landscape of human and animal nervous systems, an exchange of electrical signals between neurons is foundational to their operational dynamics. Neural stimulation stands out as a pivotal technique with a potential to profoundly influence nervous system behavior. The neural stimulation becomes particularly crucial in addressing an escalating challenge of chronic pain management, emerging as a significant national public health concern due to an increasing demand for sustained pain relief and associated risks linked to opioid use and misuse. Furthermore, neurostimulation has shown promise in treating migraines, movement disorders, and other conditions such as overactive bladder and restorative applications.

Chronic pain, a persistent medical challenge with deep historical roots, persists as a substantial burden on many users despite advances in understanding its pathophysiology. In response to this ongoing dilemma, an exploration of alternative techniques for pain relief gains significance. Neural stimulation-based approaches have demonstrated efficacy in reducing pain, presenting a promising avenue for innovative interventions.

Existing neuromodulation devices often lack a sufficient degree of personalization. Standardized settings may not cater adequately to the diverse physiological responses of the users. This limitation results in suboptimal therapeutic outcomes, as the one-size-fits-all approach does not address the unique needs of each individual. The existing neuromodulation devices employ static control mechanisms that do not adapt to dynamic changes in an individual's physiologic state. The absence of real-time or dynamic adjustments might hinder the neuromodulation device's ability to provide optimal therapy, especially when the physiological parameters of the individual fluctuate over time.

An incorporation of artificial intelligence (AI) into the neuromodulation devices is not yet widespread. Traditional control systems associated with the neuromodulation devices lack the capacity to harness the power of AI in processing complex physiologic data and dynamically adjusting treatment parameters. This limitation impedes the potential for more precise and adaptive neuromodulation therapies. The monitoring capabilities of existing neuromodulation devices are insufficient to capture a comprehensive set of relevant physiological parameters. Incomplete monitoring leads to an incomplete understanding of the user's condition, potentially compromising the effectiveness of the neuromodulation therapy.

Therefore, there is a need for a system to address the aforementioned issues by providing a comprehensive and adaptive solution to enhance the efficacy of the neuromodulation devices.

SUMMARY

This summary is provided to introduce a selection of concepts, in a simple manner, which is further described in the detailed description of the disclosure. This summary is neither intended to identify key or essential inventive concepts of the subject matter nor to determine the scope of the disclosure.

In accordance with an embodiment of the present disclosure, an artificial intelligence (AI)-based system for controlling operations of one or more neuromodulation devices based on one or more physiological parameters of one or more users is disclosed.

In an embodiment, the AI-based system comprises one or more physiological parameters sensing endpoint devices, a connectivity interface, and one or more server devices. Each neuromodulation device of the one or more neuromodulation devices comprises one or more electrode pads for inducing the electrical signals onto the defined treatment areas. The one or more electrode pads are configured to deliver the electrical signals as neuromodulation waveforms with frequencies ranging between 0.000001 hertz (Hz) to 100,000 hertz (Hz). Each neuromodulation device of the one or more neuromodulation devices comprises at least one of: an electrocardiogram (ECG) sensor, an electromyography (EMG) sensor, a skin conductivity sensor, a blood oxygen level sensor, and an impedance sensor, configured to monitor the physiological parameters of each user for determining the one or more physiological parameters. The one or more neuromodulation devices selected from a group comprise at least one of: a transcutaneous electrical nerve stimulation (TENS) device, an electromyographic stimulation device, a spinal cord stimulation device, a dorsal root ganglion stimulation device, a peripheral nerve stimulation device, and a deep brain stimulation device.

In another embodiment, the one or more physiological parameters sensing endpoint devices are operatively connected to each neuromodulation device of the one or more neuromodulation devices. The one or more physiological parameters sensing endpoint devices are configured to determine the one or more physiological parameters of each user of the one or more users. The one or more physiological parameters sensing endpoint devices are selected from a group that comprises at least one of: an accelerometer, a three-dimensional space measurement sensor, and a cutaneous sensor, configured to monitor the physiological parameters of each user for determining the one or more physiological parameters and transferred to an associated neuromodulation device of the one or more neuromodulation devices. The one or more physiological parameters comprise at least one of: heart rate, muscle activity, skin conductivity, blood oxygen levels ($SpO_2$), blood pressure, temperature, respiratory rate, electrical impedance, nerve activity, and user posture and movement.

In yet another embodiment, the connectivity interface is configured in each neuromodulation device of the one or more neuromodulation devices to operatively connect with each physiological parameters sensing endpoint device of the one or more physiological parameters sensing endpoint devices for transferring the determined one or more physiological parameters to the associated neuromodulation device of the one or more neuromodulation devices. The connectivity interface is selected from a group that comprises at least one of: a system bus, Bluetooth, wireless fidelity (Wi-Fi), Zigbee, and proprietary wireless protocols to connect the one or more neuromodulation devices with the one or more physiological parameters sensing endpoint devices and the one or more server devices.

In another embodiment, the one or more server devices are configured with one or more server applications operatively connected to the one or more neuromodulation devices. The one or more server devices comprise one or more hardware processors and a memory unit. The memory unit is operatively connected to the one or more hardware processors, wherein the memory unit comprises a set of computer-readable instructions in form of a plurality of subsystems. The plurality of subsystems are configured to be executed by the one or more hardware processors. The plurality of subsystems comprises a data-obtaining subsystem, a data-processing subsystem, an operational parameter generation subsystem, and a data recommendation subsystem.

In yet another embodiment, the data-obtaining subsystem is configured to obtain at least one of: the one or more physiological parameters from the one or more neuromodulation devices and user-centric data from one or more communication devices associated with each user of one or more users. The user-centric data comprises at least one of: user operational parameter preferences, therapy goals, and user feedback on induced electrical signals for user-centric neuromodulation therapy preferences.

In another embodiment, the data-processing subsystem is configured to process the obtained at least one of: the one or more physiological parameters and the user-centric data using at least one of: one or more artificial intelligence models and one or more machine learning models for deciphering at least one of: multifaceted patterns, correlations, and trends within at least one of: the one or more physiological parameters and the user-centric data. The at least one of: the one or more artificial intelligence models and the one or more machine learning models comprises at least one of: supervised learning models, unsupervised learning models, reinforcement learning models, time series analysis models, and natural language processing (NLP) models.

The supervised learning models comprise at least one of: neural networks, support vector machines (SVM), random forests, and gradient boosting machines, to classify the one or more physiological parameters based on historical treatment data to determine one or more user-centric operational parameters. The unsupervised learning models comprise at least one of: a K-means clustering, a hierarchical clustering analysis, and a principal component analysis (PCA), to identify patterns in the one or more physiological parameters for classifying the one or more physiological parameters. The reinforcement learning models comprise at least one of: a Q-learning model and Policy gradient methods, to optimize the user-centric neuromodulation therapy preferences through the user feedback. The time series analysis models comprise at least one of: Recurrent Neural Networks (RNNs), Long Short-Term Memory (LSTM) networks, and autoregressive integrated moving average (ARIMA) models, to analyze and predict trends in the one or more physiological parameters over time. The natural language processing (NLP) models are configured to process the user-centric data to determine at least one of: the user operational parameter preferences, the therapy goals, and the user feedback for determining the one or more user-centric operational parameters.

In yet another embodiment, the operational parameter generation subsystem is configured to generate the one or more user-centric operational parameters in each neuromodulation device of the one or more neuromodulation devices using at least one of: the one or more artificial intelligence models and the one or more machine learning models. The generation of the one or more user-centric operational parameters based on the processed at least one of: the one or more physiological parameters and the user-centric data, for optimizing user-centric neuromodulation therapy preferences. The one or more user-centric operational parameters comprise at least one of: a pulse width, a stimulation amplitude, a stimulation frequency, a stimulation intensity, and an impedance, associated with the induced electrical signals.

In another embodiment, the data recommendation subsystem is configured to transmit the generated one or more user-centric operational parameters to the associated neuromodulation device of the one or more neuromodulation devices for controlling operations of the one or more neuromodulation devices. The controlling operations comprise inducing electrical signals through the associated neuromodulation device of the one or more neuromodulation devices, on defined treatment areas on a body of an associated user of the one or more users based on the one or more user-centric operational parameters.

In yet another embodiment, the AI-based system further comprises a plurality of modules. The plurality of modules comprises a learning module, a survey module, a community module, a logging module, a provider identification module, an educational resource providing module, a neuromodulation products recommendation module, a remote therapy monitoring (RTM) module, a remote patient monitoring (RPM) module, and a dashboard module.

In another embodiment, the learning module is configured with an adaptive learning model to continuously optimize at least one of: the one or more artificial intelligence models and the one or more machine learning models based on analyzing real-time at least one of: the one or more physiological parameters and the user-centric data. The survey module is configured to provide a pre-defined set of queries to one or more users during at least one of: a pre-treatment phase and a post-treatment phase for obtaining at least one of: visual analog score (VAS) results, patient global impression of change (PGIC) results, Patient-Reported Outcomes Measurement Information System (PROMIS) score, Oxygen Desaturation Index (ODI), clinical trial data, and real-world data, to continuously update and optimize at least one of: the one or more artificial intelligence models and the one or more machine learning models.

The community module is configured to connect the one or more users receiving a neuromodulation therapy to a network of cohort users for sharing at least one of: experiences, progress, and feedback, fostering a collaborative environment through at least one of: comments, follows, likes, and group interactions. The logging module is configured to generate log data for each user of the one or more users based on the user-centric neuromodulation therapy preferences, wherein the log data comprises at least one of: a therapy duration, therapy timelines, and the one or more user-centric operational parameters.

The provider identification module is configured to connect the one or more users with one or more healthcare providers based on one or more attributes that comprise at least one of: location, proficiency in the neuromodulation therapy, and acquaintance with the one or more neuromodulation devices. The educational resource providing module is configured to provide one or more educational resources to at least one of: the one or more users and the one or more healthcare providers, wherein the one or more educational resources comprise at least one of: instructional videos, neuromodulation therapy documentations, and one or more manuals related to at least one of: the neuromodulation therapy and the one or more neuromodulation devices.

The neuromodulation products recommendation module is configured to depict at least one of: one or more advertisements and sponsored content on the one or more communication devices associated with each user of one or more users, for providing product suggestions related to the neuromodulation therapy. The remote therapy monitoring (RTM) module is configured to monitor the real-time efficacy of the neuromodulation therapy by analyzing the obtained user-centric data for generating the one or more user-centric operational parameters.

The remote patient monitoring (RPM) module is configured to analyze obtained at least one of: the one or more physiological parameters and the user-centric data in real-time for altering the one or more user-centric operational parameters in the associated neuromodulation device. The dashboard module is operatively connected to the one or more communication devices. The dashboard module is configured to display visual representations related to at least one of: neuromodulation therapy outcomes, real-time one or more physiological parameters, one or more user-centric operational parameters, and invoice data, for providing information to at least one of: the one or more users and the one or more healthcare providers regarding the neuromodulation therapy.

According to another embodiment of the present disclosure, an AI-based method for controlling the operations of the one or more neuromodulation devices based on the one or more physiological parameters of the one or more users. In the first step, the AI-based method includes determining, by the one or more physiological parameters sensing endpoint devices, the one or more physiological parameters of each user of the one or more users. In the next step, the AI-based method includes transferring, by the connectivity interface, the determined the one or more physiological parameters to the associated neuromodulation device of the one or more neuromodulation devices from the one or more physiological parameters sensing endpoint devices.

In the next step, the AI-based method includes obtaining, by the one or more server devices through the data-obtaining subsystem, at least one of: the one or more physiological parameters from the one or more neuromodulation devices and the user-centric data from the one or more communication devices associated with each user of one or more users. In the next step, the AI-based method includes processing, by the one or more server devices through the data-processing subsystem, the obtained at least one of: the one or more physiological parameters and the user-centric data using at least one of: the one or more artificial intelligence models and the one or more machine learning models for deciphering at least one of: multifaceted patterns, correlations, and trends within at least one of: the one or more physiological parameters and the user-centric data.

In the next step, the AI-based method includes generating, by the one or more server devices through the operational parameter generation subsystem, the one or more user-centric operational parameters in each neuromodulation device of the one or more neuromodulation devices using at least one of: the one or more artificial intelligence models and the one or more machine learning models, based on the processed at least one of: the one or more physiological parameters and the user-centric data, for optimizing the user-centric neuromodulation therapy preferences. In the next step, the AI-based method includes transmitting, by the one or more server devices through the data recommendation subsystem, the generated one or more user-centric operational parameters to the associated neuromodulation device of the one or more neuromodulation devices for controlling operations of the one or more neuromodulation devices. The controlling operations comprise inducing the electrical signals through the associated neuromodulation device of the one or more neuromodulation devices, on the defined treatment areas on the body of the associated user of the one or more users based on the one or more user-centric operational parameters.

According to another embodiment of the present disclosure, a non-transitory computer-readable storage medium storing computer-executable instructions that, when executed by the one or more servers, cause the one or more servers to perform the one or more actions for controlling the operations of the one or more neuromodulation devices based on the one or more physiological parameters of the one or more users. The one or more actions comprising: a) determining the one or more physiological parameters of each user of the one or more users, b) transferring the determined one or more physiological parameters to the associated neuromodulation device of the one or more neuromodulation devices from the one or more physiological parameters sensing endpoint devices, c) obtaining at least one of: the one or more physiological parameters from the one or more neuromodulation devices and the user-centric data from the one or more communication devices associated with each user of one or more users, d) processing the obtained at least one of: the one or more physiological parameters and the user-centric data using at least one of: the one or more artificial intelligence models and the one or more machine learning models for deciphering at least one of: the multifaceted patterns, the correlations, and the trends within at least one of: the one or more physiological parameters and the user-centric data, e) generating the one or more user-centric operational parameters in each neuromodulation device of the one or more neuromodulation devices using at least one of: the one or more artificial intelligence models and the one or more machine learning models, based on the processed at least one of: the one or more physiological parameters and the user-centric data, for optimizing the user-centric neuromodulation therapy preferences, and f) transmitting the generated one or more user-centric operational parameters to the associated neuromodulation device of the one or more neuromodulation devices for controlling operations of the one or more neuromodulation devices. The controlling operations comprise inducing the electrical signals through the associated neuromodulation device of the one or more neuromodulation devices, on the defined treatment areas on the body of the associated user of the one or more users based on the one or more user-centric operational parameters.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF DRAWINGS

The disclosure will be described and explained with additional specificity and detail with the accompanying figures in which.

Figure 1:
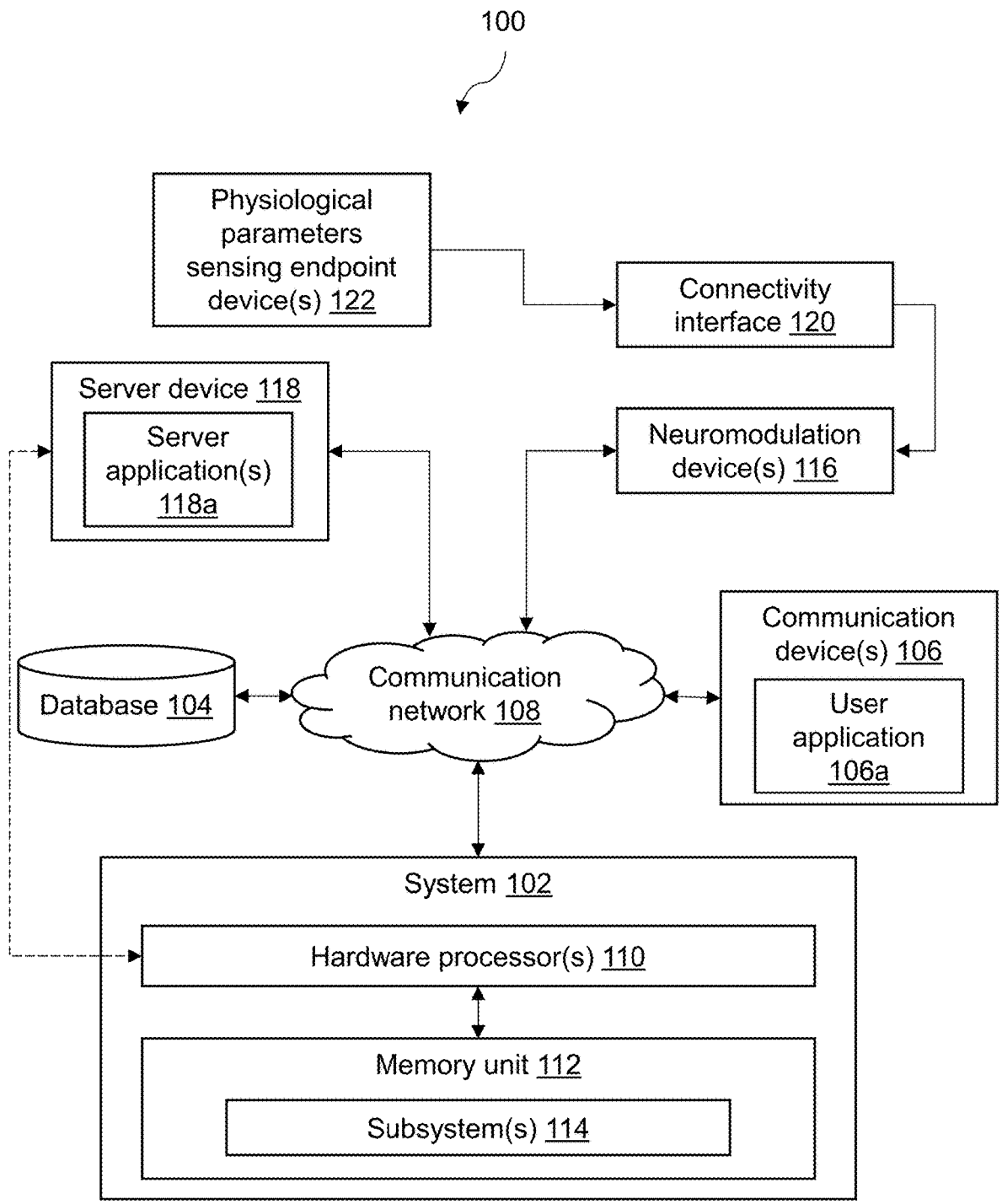
FIG. 1 illustrates an exemplary block diagram representation of a network architecture of an artificial intelligence (AI)-based system for controlling operations of one or more neuromodulation devices based on one or more physiological parameters of one or more users, in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION OF THE DISCLOSURE

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure. It will be understood by those skilled in the art that the foregoing general description and the following detailed description are exemplary and explanatory of the disclosure and are not intended to be restrictive thereof.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

The terms "comprise", "comprising", or any other variations thereof, are intended to cover a non-exclusive inclusion, such that one or more devices or sub-systems or elements or structures or components preceded by "comprises . . . a" does not, without more constraints, preclude the existence of other devices, sub-systems, additional sub-modules. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

A computer system (standalone, client or server computer system) configured by an application may constitute a "module" (or "subsystem") that is configured and operated to perform certain operations. In one embodiment, the "module" or "subsystem" may be implemented mechanically or electronically, so a module include dedicated circuitry or logic that is permanently configured (within a special-purpose processor) to perform certain operations. In another embodiment, a "module" or "subsystem" may also comprise programmable logic or circuitry (as encompassed within a general-purpose processor or other programmable processor) that is temporarily configured by software to perform certain operations.

Accordingly, the term "module" or "subsystem" should be understood to encompass a tangible entity, be that an entity that is physically constructed permanently configured (hardwired) or temporarily configured (programmed) to operate in a certain manner and/or to perform certain operations described herein.

Referring now to the drawings, and more particularly to FIG. 1 through FIG. 6, where similar reference characters denote corresponding features consistently throughout the figures, there are shown preferred embodiments, and these embodiments are described in the context of the following exemplary system and/or method.

FIG. 1 illustrates an exemplary block diagram representation of a network architecture 100 of an artificial intelligence (AI)-based system 102 for controlling operations of one or more neuromodulation devices 116 based on one or more physiological parameters of one or more users, in accordance with an embodiment of the present disclosure.

According to an embodiment of the present disclosure, FIG. 1, the network architecture 100 may include the AI-based system 102, a database 104, and one or more communication devices 106. The AI-based system 102 may be communicatively coupled to the database 104, and the one or more communication devices 106 via a communication network 108. The communication network 108 may be a wired communication network and/or a wireless communication network. The database 104 may include, but is not limited to, storing, and managing data associated with various aspects of the AI-based system 102. This data includes, but is not limited to, information related to the operation and performance of the AI-based system 102, data generated by one or more neuromodulation devices 116, user-specific one or more physiological parameters, historical treatment data, and any other pertinent information essential for the functionality of the AI-based system 102. The database 104 may be any kind of database such as, but are not limited to, relational databases, Non-relational databases, graph databases, document databases, dedicated databases, dynamic databases, monetized databases, scalable databases, cloud databases, distributed databases, any other databases, and a combination thereof.

In an exemplary embodiment, the one or more communication devices 106 serve as interfaces for one or more users, individuals, clinicians, one or more healthcare providers, and other stakeholders to interact with the AI-based system 102. Through these one or more communication devices 106, the one or more users, the individuals, the clinicians, the one or more healthcare providers, and the other stakeholder's access and input relevant data, receive information about a neuromodulation therapy and potentially adjust one or more user-centric operational parameters based on the insights provided by the AI-based system 102. The one or more communication devices 106 may be used to obtain user-centric data and/or receive output to/from the AI-based system 102, and/or to the database 104, respectively. The one or more communication devices 106 may be configured with one or more user interfaces to interact with the AI-based system 102 and/or with the database 104 for seamless and user-friendly engagement. The one or more user interfaces are designed to provide the one or more users, the individuals, the clinicians, the one or more healthcare providers, and the other stakeholders with intuitive means to access and navigate the functionalities offered by the AI-based system 102.

Through these one or more user interfaces, the one or more users input relevant user-centric data, retrieve information about the neuromodulation therapy, and potentially make adjustments to one or more user-centric operational parameters based on the insights provided by the AI-based system 102. The user interfaces function as a gateway for communication, enabling stakeholders to stay informed about the AI-based system 102 operations, view historical treatment data, and participate in the optimization of the neuromodulation therapy. The one or more communication devices 106 may include, but is not limited to, a mobile device, a smartphone, a personal digital assistant (PDA), a tablet computer, a phablet computer, a wearable computing device, a virtual reality/augmented reality (VR/AR) device, a laptop, a desktop, and the like.

In an exemplary embodiment, the one or more communication devices 106 is configured with a user application 106a. The user application 106a is configured to serve as an interactive platform, facilitating smooth communication and user engagement with the AI-based system 102 and the database 104. The user application 106a enables the one or more users to access the features and functionalities of the AI-based system 102 and retrieve relevant information stored in the database 104. The user application 106a allows the one or more users to input the user-centric data, such as, but not limited to, at least ono of: user operational parameter preferences, therapy goals, user feedback on induced electrical signals for the user-centric neuromodulation therapy preferences, and the like, contributing to a comprehensive dataset for analysis. The user application 106a presents data and insights generated by the AI-based system 102 in a visually comprehensible manner, enhancing the user's ability to understand and interpret the information related to the neuromodulation therapy. The user application 106a enables the one or more users, under appropriate authorization, to make adjustments to one or more user-centric operational parameters or settings based on the recommendations or insights provided by the AI-based system 102. Keep the one or more users informed by delivering at least one of: one or more notifications, one or more alerts, and one or more updates related to the operation and performance of the one or more neuromodulation devices 116 and any relevant AI-based system 102 developments.

Further, the AI-based system 102 may be implemented by way of a single device or a combination of multiple devices that may be operatively connected or networked together. The AI-based system 102 may be implemented in hardware or a suitable combination of hardware and software. The AI-based system 102 includes one or more hardware processors 110, and a memory unit 112. The memory unit 112 may include a plurality of subsystems 114. The AI-based system 102 may be a hardware device including the one or more hardware processors 110 executing machine-readable program instructions for dynamically recommending a course of action sequences for managing the neuromodulation therapy and periodically monitoring the one or more physiological parameters of each user of the one or more users. The machine-readable program instructions, stored in the memory unit 112, leverage artificial intelligence and data analytics to interpret the complex interplay of these one or more physiological parameters.

The primary function of the AI-based system 102 is to generate dynamic recommendations for adjusting and optimizing the operations of the one or more neuromodulation devices 116. These recommendations are personalized based on each user's unique physiological responses, ensuring a tailored and responsive approach to the neuromodulation therapy. The one or more hardware processors 110 facilitate the swift and accurate execution of these recommendations, contributing to the overall effectiveness of neuromodulation therapy.

In an exemplary embodiment, the one or more neuromodulation devices 116 is configured to administer therapeutic interventions based on the dynamic recommendations generated by the AI-based system 102. The one or more neuromodulation devices 116, which may include, but not limited to, a transcutaneous electrical nerve stimulation (TENS), an electromyographic stimulation device, a spinal cord stimulation device, a dorsal root ganglion stimulation device, a peripheral nerve stimulation device, deep brain stimulation devices and other similar medical devices, for inducing electrical signals onto defined treatment areas to address different therapeutic paradigms, including pain relief, muscle strengthening, and relaxation. The pain relief may comprise at least one of: musculoskeletal pain, nociceptive pain, acute and chronic pain, neuropathic pain, fibromyalgia, and the like. The one or more neuromodulation devices 116, in a non-limiting embodiment, may function as wireless devices, establishing communication with the AI-based system 102 through the communication network 108. This communication network 108 enhances flexibility and accessibility, allowing the one or more users to interact with and manage the one or more neuromodulation devices 116 remotely. Moreover, the one or more neuromodulation devices 116 is equipped with various features to optimize therapeutic outcomes.

In an exemplary embodiment, the one or more neuromodulation devices 116 is able to induce the electrical signals ranging from high-frequency to low-frequency signals, catering to diverse therapeutic needs. The transmission of the electrical signals is facilitated through one or more electrode pads adhering to defined treatment areas on the body of an associated user within the one or more users. The body of the associated user may undergo stimulation at diverse anatomical points including, but not limited to, the subdural space, specific points on the skin surface, the epidural space, and the like. This versatility in stimulation locations allows for a targeted and individualized approach to the administration of the neuromodulation therapy. The selection of stimulation points may be tailored based on the specific therapeutic goals, the nature of the pain or condition being addressed, and the associated user's unique physiological responses. By stimulating at varying anatomical points, the one or more neuromodulation devices 116 aims to optimize the efficacy of the therapy and provide a personalized treatment experience for the one or more users.

In an exemplary embodiment, each neuromodulation device of the one or more neuromodulation devices inbuilt with one or more sensors for collecting the one or more physiological parameters. The one or more sensors may comprise at least one of: an electrocardiogram (ECG) sensor, an electromyography (EMG) sensor, a skin conductivity sensor, a blood oxygen level sensor, and an impedance sensor, configured to monitor the physiological parameters of each user for determining the one or more physiological parameters. The ECG sensor is configured to track an electrical activity of heart of the associated user. The EMG sensor is configured to measure electrical activity produced by muscles of the associated user, often used to detect nerve activity. The skin conductivity sensor is configured to determine a skin conductivity (also known as galvanic skin response) changes due to sweating. The blood oxygen level sensor is configured to determine oxygen saturation in the blood of each user. The impedance sensor is configured to determine a resistance encountered by the electrical signals as they pass through tissues, which may be used to monitor how well the electrical signals are delivered.

Moreover, the one or more electrode pads associated with each neuromodulation device 116 are configured to deliver the electrical signals as neuromodulation waveforms with frequencies ranging between 0.000001 hertz (Hz) to 100,000 hertz (Hz). This may be achieved through continuous duty cycling, incorporating frequencies such as 5 Hz and 30 Hz in an uninterrupted manner. This approach, as exemplified in the practices with Medtronic and Nevro devices, reflects the adaptability of the neuromodulation devices in accommodating various waveform configurations for pain management. For instance, the one or more neuromodulation devices 116 may administer waveform frequencies ranging from 300 Hz to 1200 Hz. In one exemplary embodiment, the waveform frequencies 5 Hz and 30 Hz are applied with a subthreshold of 300 ms. In another exemplary embodiment, a sequential application involving 300 Hz followed by a pattern consisting of 5 Hz for 300 ms and 30 Hz for 300 ms. This sequence is applied for 15 minutes followed by a 15-minute off period.

Further, each neuromodulation device 116 is configured with a connectivity interface 120. The connectivity interface 120 configured to operatively connect each neuromodulation device 116 with each physiological parameters sensing endpoint device 122 of one or more physiological parameters sensing endpoint devices 122. The one or more physiological parameters sensing endpoint devices 122 are external sensors configured to determine the one or more physiological parameters of each user of the one or more users. The connectivity interface 120 is configured to each neuromodulation device 116 to each physiological parameters sensing endpoint device 122 of the one or more physiological parameters sensing endpoint devices 122 for transferring the determined one or more physiological parameters to the associated neuromodulation device 116 of the one or more neuromodulation devices 116. The connectivity interface 120 is selected from a group comprises, but not limited to, at least one of: a system bus, Bluetooth, wireless fidelity (Wi-Fi), Zigbee, proprietary wireless protocols, and the like. The connectivity interface 120 is configured to connect the one or more neuromodulation devices 116 with the one or more physiological parameters sensing endpoint devices 122 and one or more server devices 118.

In an exemplary embodiment, the one or more physiological parameters sensing endpoint devices 122 are selected from a group comprises at least one of: an accelerometer, a three-dimensional space measurement sensor, and a cutaneous sensor, configured to monitor the physiological parameters of each user for determining the one or more physiological parameters and transferred to the associated neuromodulation device 116. The accelerometer is configured to monitor at least one of: motion, posture, and physical activity of the associated user. The three-dimensional space measurement sensor is configured to track body orientation and movement in three-dimensional space, often used in posture correction and rehabilitation contexts. The cutaneous sensor is configured to monitor skin conductivity of the associated user. Furthermore, the one or more physiological parameters comprise at least one of: heart rate, muscle activity, skin conductivity, blood oxygen levels ($SpO_2$), blood pressure, temperature, respiratory rate, electrical impedance, nerve activity, and user posture and movement.

In an exemplary embodiment, the AI-based system 102 and the one or more neuromodulation devices 116 operatively connect the one or more server devices 118 via the communication network 108. The one or more server devices 118 are configured with one or more server applications 118a. The one or more server devices 118 and the one or more server applications 118a play integral roles in the overall functionality of the AI-based system 102, facilitating communication, data processing, and the execution of the plurality of subsystems 114 by one or more hardware processors 110. The one or more server devices 118 serve as a central hub within the network architecture 100, overseeing the coordination and execution of different components. In one non-limiting implementation, the one or more server devices 118 represent a series of servers configured to distribute various aspects of the one or more neuromodulation devices 116. Alternatively, the one or more server devices 118 are configured to provide cloud-based services accessible to the one or more communication devices 106, and the one or more neuromodulation devices 116. The one or more server applications 118a, residing on the one or more server devices 118, are a comprehensive software module designed to render various functionalities and services to the one or more communication devices 106, and the one or more neuromodulation devices 116.

In an exemplary embodiment, the communication networks 108 may be, but not limited to, a wired communication network and/or a wireless communication network. The wired communication network may comprise, but not limited to, at least one of: Ethernet connections, Fiber Optics, Power Line Communications (PLCs), Serial Communications, Coaxial Cables, Quantum Communication, Advanced Fiber Optics, Hybrid Networks, and the like. The wireless communication network may comprise, but not limited to, at least one of: wireless fidelity (wi-fi), cellular networks (including fourth generation (4G) technologies and fifth generation (5G) technologies), Bluetooth, ZigBee, long-range wide area network (LoRaWAN), satellite communication, radio frequency identification (RFID), 6G (sixth generation) networks, advanced IoT protocols, mesh networks, non-terrestrial networks (NTNs), near field communication (NFC), and the like.

The one or more hardware processors 110 may include, for example, microprocessors, microcomputers, microcontrollers, digital signal processors, central processing units, state machines, logic circuits, and/or any devices that manipulate data or signals based on operational instructions. Among other capabilities, the one or more hardware processors 110 may fetch and execute computer-readable instructions in the memory unit 112 operationally coupled with the AI-based system 102 for performing tasks such as data processing, input/output processing, and/or any other functions. Any reference to a task in the present disclosure may refer to an operation being or that may be performed on data.

Though few components and subsystems are disclosed in FIG. 1, there may be additional components and subsystems which is not shown, such as, but not limited to, ports, routers, repeaters, firewall devices, network devices, databases, network attached storage devices, servers, assets, machinery, instruments, facility equipment, emergency management devices, image capturing devices, any other devices, and combination thereof. The person skilled in the art should not be limiting the components/subsystems shown in FIG. 1. Although FIG. 1 illustrates the AI-based system 102, and the one or more communication devices 106 connected to the database 104, one skilled in the art can envision that the AI-based system 102, and the one or more communication devices 106 may be connected to several user devices located at various locations and several databases via the communication network 108.

Those of ordinary skilled in the art will appreciate that the hardware depicted in FIG. 1 may vary for particular implementations. For example, other peripheral devices such as an optical disk drive and the like, local area network (LAN), wide area network (WAN), wireless (e.g., wireless-fidelity (Wi-Fi)) adapter, graphics adapter, disk controller, input/output (I/O) adapter also may be used in addition or place of the hardware depicted. The depicted example is provided for explanation only and is not meant to imply architectural limitations concerning the present disclosure.

Those skilled in the art will recognize that, for simplicity and clarity, the full structure and operation of all data processing systems suitable for use with the present disclosure are not being depicted or described herein. Instead, only so much of the AI-based system 102 as is unique to the present disclosure or necessary for an understanding of the present disclosure is depicted and described. The remainder of the construction and operation of the AI-based system 102 may conform to any of the various current implementations and practices that were known in the art.

Figure 2A:
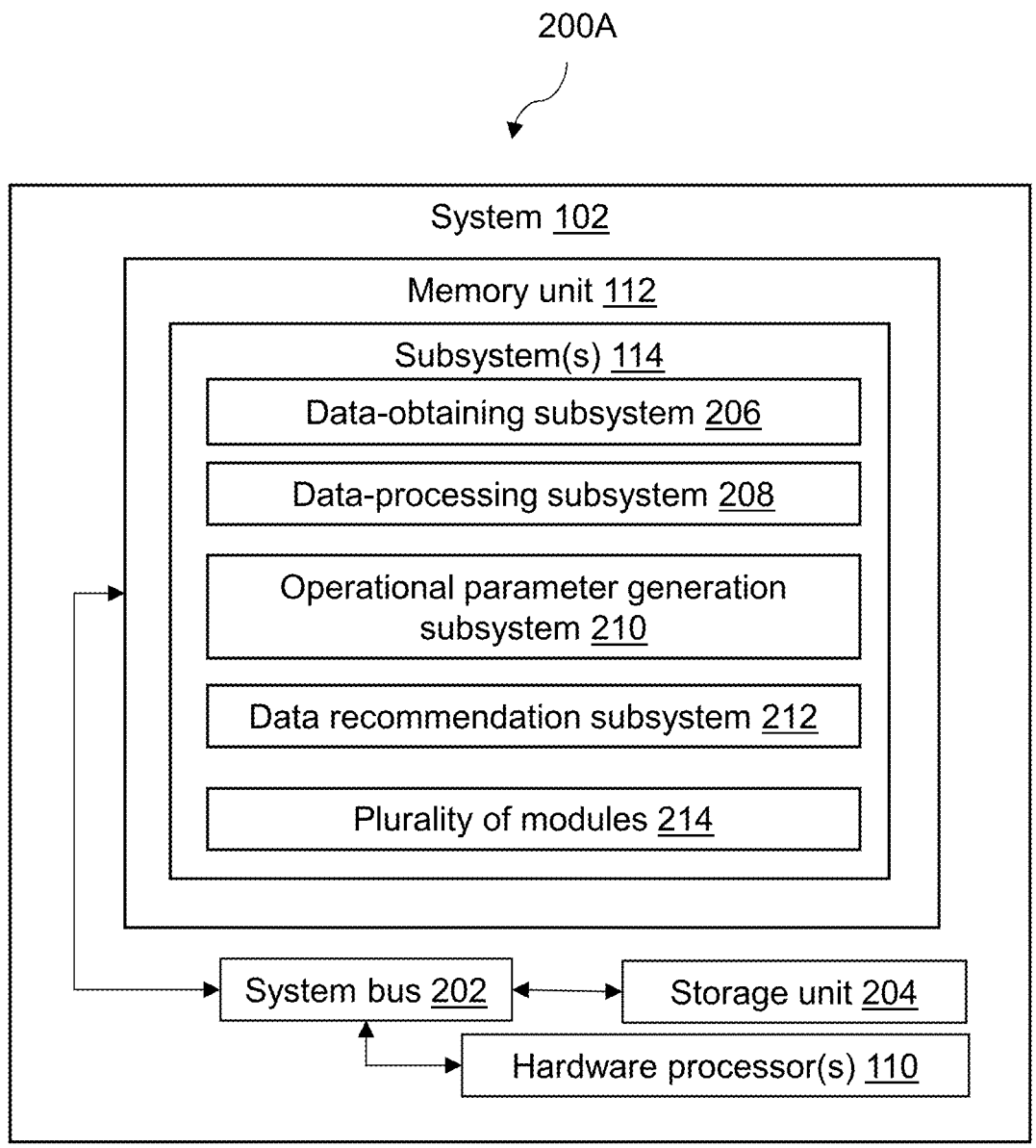
FIG. 2A illustrates an exemplary block diagram representation of the AI-based system as shown in FIG. 1 for controlling the operations of the one or more neuromodulation devices based on the one or more physiological parameters of the one or more users, in accordance with an embodiment of the present disclosure.

FIG. 2A illustrates an exemplary block diagram representation 200A of the AI-based system 102 as shown in FIG. 1 for controlling the operations of the one or more neuromodulation devices 116 based on the one or more physiological parameters of the one or more users, in accordance with an embodiment of the present disclosure.

Figure 2B:
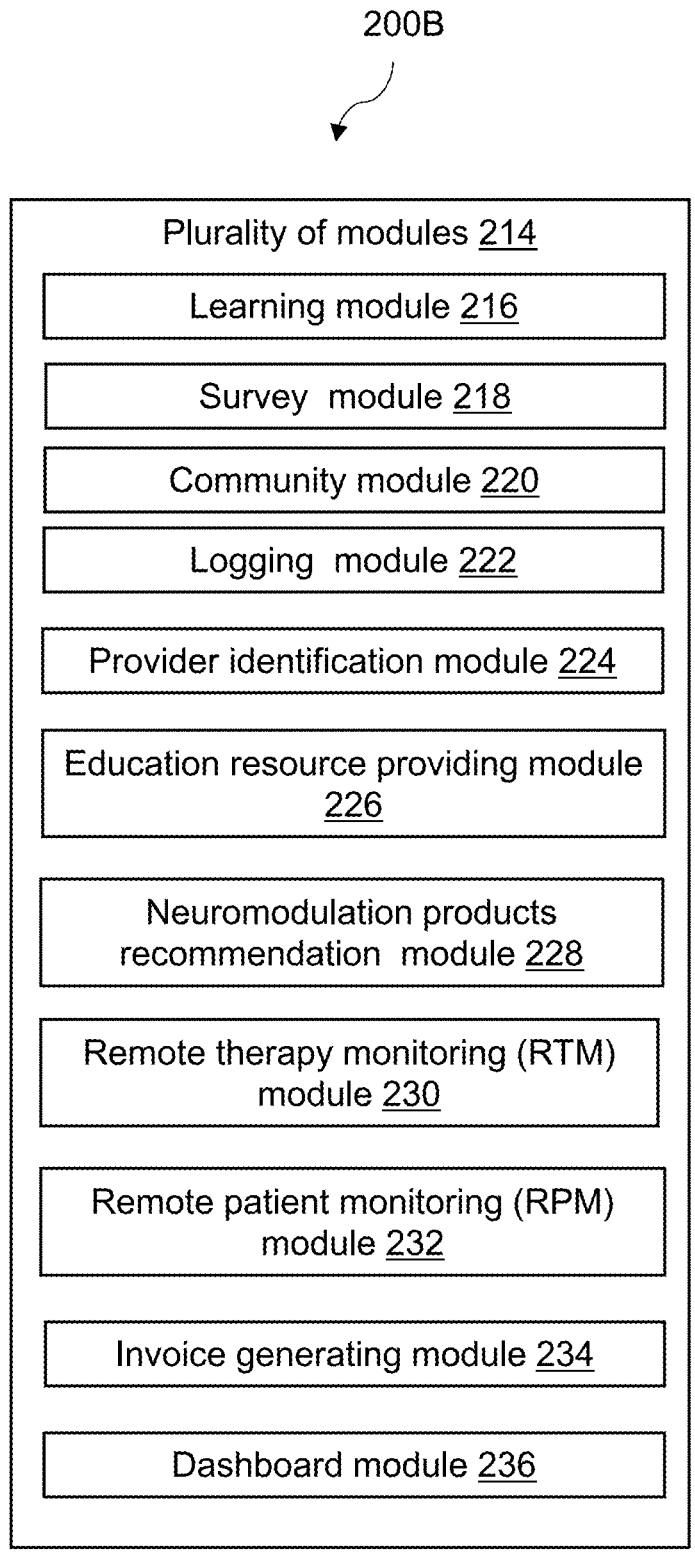
FIG. 2B illustrates an exemplary block diagram representation of the AI-based system configured with a plurality of modules, in accordance with an embodiment of the present disclosure.

FIG. 2B illustrates an exemplary block diagram representation 200B of the AI-based system 102 configured with a plurality of modules 214, in accordance with an embodiment of the present disclosure.

Figure 2C:
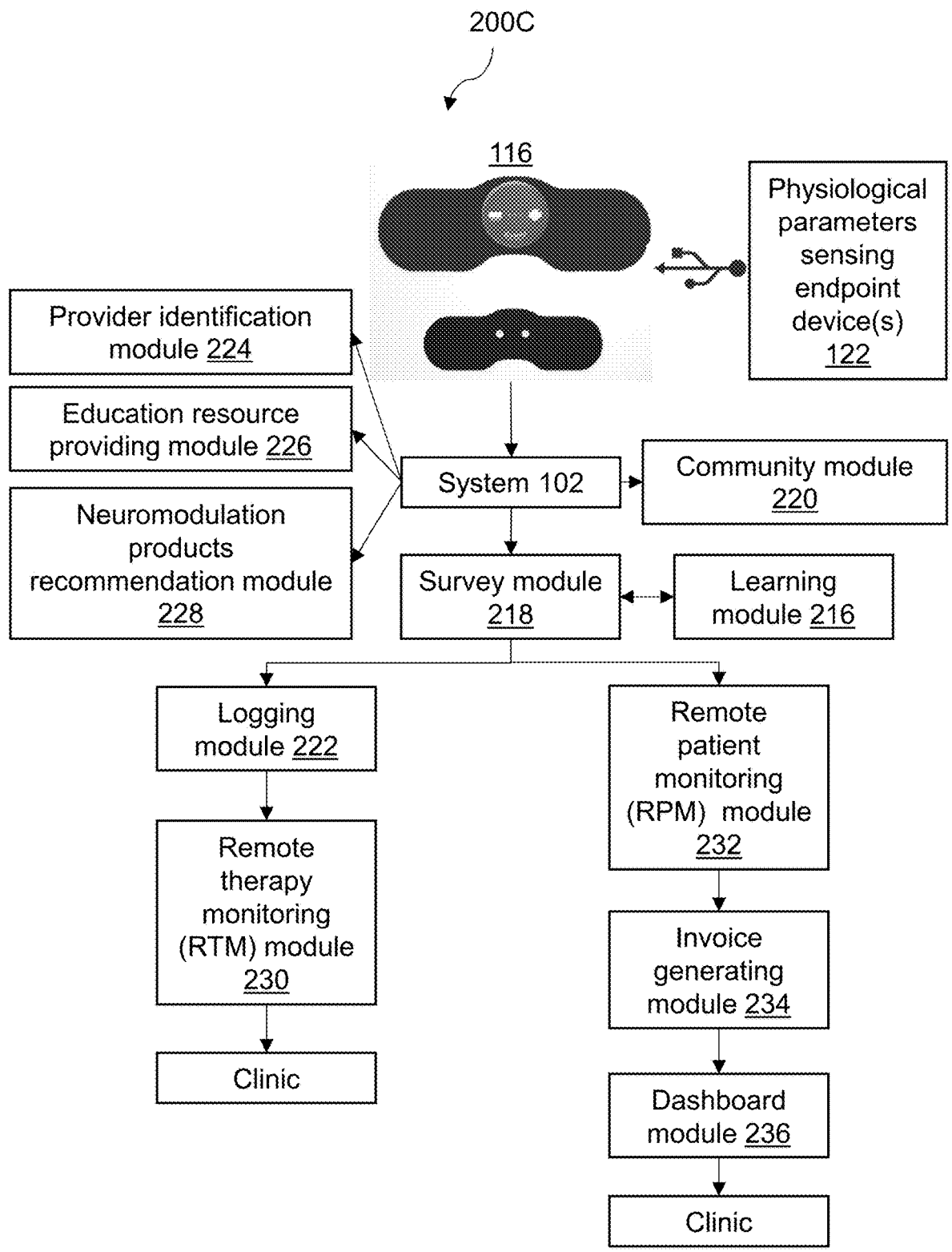
FIG. 2C illustrates an exemplary flow chart depicting the plurality of modules interacting with the one or more neuromodulation devices, in accordance with an embodiment of the present disclosure.

FIG. 2C illustrates an exemplary flow chart 200C depicting the plurality of modules 214 interacting with the one or more neuromodulation devices 116, in accordance with an embodiment of the present disclosure.

In an exemplary embodiment, the AI-based system 102 (hereinafter referred to as the system 102). The system 102 comprises the one or more hardware processors 110, the memory unit 112, and a storage unit 204. The one or more hardware processors 110, the memory unit 112, and the storage unit 204 are communicatively coupled through the system bus 202 or any similar mechanism. The system bus 202 facilitates the efficient exchange of information and instructions, enabling the coordinated operation of the system 102. The system bus 202 may be implemented using various technologies including, but not limited to, parallel buses, serial buses, or high-speed data transfer interfaces such as, but not limited to, at least one of a: universal serial bus (USB), peripheral component interconnect express (PCIe), and similar standards. The memory unit 112 is operatively coupled to the one or more hardware processors 110. The memory unit 112 comprises the plurality of subsystems 114 in the form of programmable instructions executable by the one or more hardware processors 110.

The plurality of subsystems 114 comprises a data-obtaining subsystem 206, a data-processing subsystem 208, an operational parameter generation subsystem 210, a data recommendation subsystem 212, and the plurality of modules 214. The one or more server application 118a serves as the central control hub, overseeing the execution of the plurality of subsystems 114. The one or more server application 118a manages device platform control, integrates learning modules, facilitates community interactions, controls data curation and analysis, identifies providers, supports education modules, manages commercials, and oversees real-time and remote monitoring, billing, and dashboard functionality.

The one or more hardware processors 110, as used herein, means any type of computational circuit, such as, but not limited to, a microprocessor unit, microcontroller, complex instruction set computing microprocessor unit, reduced instruction set computing microprocessor unit, very long instruction word microprocessor unit, explicitly parallel instruction computing microprocessor unit, graphics processing unit, digital signal processing unit, or any other type of processing circuit. The one or more hardware processors 110 may also include embedded controllers, such as generic or programmable logic devices or arrays, application-specific integrated circuits, single-chip computers, and the like.

The memory unit 112 may be a non-transitory volatile memory and a non-volatile memory. The memory unit 112 may be coupled to communicate with the one or more hardware processors 110, such as being a computer-readable storage medium. The one or more hardware processors 110 may execute machine-readable instructions and/or source code stored in the memory unit 112. A variety of machine-readable instructions may be stored in and accessed from the memory unit 112. The memory unit 112 may include any suitable elements for storing data and machine-readable instructions, such as read-only memory, random access memory, erasable programmable read-only memory, electrically erasable programmable read-only memory, a hard drive, a removable media drive for handling compact disks, digital video disks, diskettes, magnetic tape cartridges, memory cards, and the like. In the present embodiment, the memory unit 112 includes the plurality of subsystems 114 stored in the form of machine-readable instructions on any of the above-mentioned storage media and may be in communication with and executed by the one or more hardware processors 110.

The storage unit 204 may be a cloud storage or a database such as those shown in FIG. 1. The storage unit 204 may store, but is not limited to, recommending a course of action sequences, applications, application links, application name, application description, application meta-data, application identifier, display name of the one or more applications, short textual description, a universal resource locator (URL) of the one or more applications, and a list of parameters corresponding to application context, generated recommending course of action sequences, one or more clickable elements, completion status of initiated user action through recommended course of action sequences, feedback loops, feedback from the one or more users, one or more query parameters, additional query parameters, deep integration parameters, up-sell/x-sell product links, tracked user click-through rates, any other data, and combinations thereof. The storage unit 204 may be any kind of database such as, but are not limited to, relational databases, dedicated databases, dynamic databases, monetized databases, scalable databases, cloud databases, distributed databases, any other databases, and a combination thereof.

In an exemplary embodiment, the data-obtaining subsystem 206 is configured to obtain at least one of: the one or more physiological parameters from the one or more neuromodulation devices 116 and user-centric data from one or more communication devices 106 associated with each user of one or more users. The one or more physiological parameters refer to measurable indicators of the user's bodily functions that are monitored by the neuromodulation devices 116. The one or more physiological parameters are critical in assessing the user's current physiological state and determining how the body is responding to the neuromodulation therapy. The data obtained from these one or more physiological parameters may include, but is not limited to, the heart rate, the muscle activity, the skin conductivity, the blood oxygen levels ($SpO_2$), and other relevant physiological metrics. The ability of the data-obtaining subsystem 206 to capture these one or more physiological parameters allows the system 102 to continuously monitor the associated user's physical responses and adjust the neuromodulation therapy accordingly.

In addition to one or more physiological parameters, the data-obtaining subsystem 206 is configured to obtain the user-centric data from the one or more communication devices 106. The user-centric data comprises at least one of: user operational parameter preferences, therapy goals, and user feedback on induced electrical signals for user-centric neuromodulation therapy preferences. The therapy goals are the objectives that the associated user or their healthcare provider aims to achieve through the neuromodulation therapy. These therapy goals may vary depending on the condition being treated, such as pain reduction, muscle strengthening, or improved nerve function. By understanding the therapy goals, the system 102 may align its operational parameters to support these outcomes effectively. The user feedback on induced electrical signals is essential for evaluating the effectiveness and comfort of the neuromodulation therapy. This user feedback may include the associated user's subjective experience of the neuromodulation therapy, such as sensations of relief, discomfort, or any adverse effects. The system 102 utilizes this user feedback to make real-time adjustments to the neuromodulation therapy, ensuring that the medication is both effective and tolerable for the one or more users.

In an exemplary embodiment, the data-processing subsystem 208 is configured to process the obtained at least one of: the one or more physiological parameters and the user-centric data. The data-processing subsystem 208 utilizes advanced computational techniques, specifically at least one of: one or more artificial intelligence models and one or more machine learning models to decipher complex information from at least one of: the one or more physiological parameters and the user-centric data. The processing conducted by the data-processing subsystem 208 involves identifying at least one of: multifaceted patterns, correlations, and trends within at least one of: the one or more physiological parameters and the user-centric data. The processing of the one or more physiological parameters and the user-centric data may reveal significant insights into the user's physiological responses to the neuromodulation therapy and the effectiveness of the neuromodulation therapy in meeting the user's specific needs and goals. For instance, the system 102 might detect trends in heart rate variability in response to the one or more user-centric operational parameters, or it might correlate user feedback on discomfort with specific therapy settings, thereby enabling more precise adjustments to be made in the one or more user-centric operational parameters.

To achieve this, the data-processing subsystem 208 employs at least one of: the one or more artificial intelligence models and the one or more machine learning models. The one or more artificial intelligence models and the one or more machine learning models used by the system 102 are specifically tailored to handle the complex and dynamic nature of the data. The at least one of: the one or more artificial intelligence models and the one or more machine learning models comprises at least one of: supervised learning models, unsupervised learning models, reinforcement learning models, time series analysis models, and natural language processing (NLP) models.

In an exemplary embodiment, the supervised learning models comprise, but not limited to, at least one of: neural networks, support vector machines (SVM), random forests, gradient boosting machines, and the like. The supervised learning models are configured to classify the one or more physiological parameters based on historical treatment data to determine the one or more user-centric operational parameters. The unsupervised learning models comprise, but not limited to, at least one of: a K-means clustering, a hierarchical clustering analysis, a principal component analysis (PCA), and the like. The unsupervised learning models are configured to identify patterns in the one or more physiological parameters for classifying the one or more physiological parameters. The reinforcement learning models comprise, but not limited to, at least one of: a Q-learning model, Policy gradient methods, and the like. The reinforcement learning models are configured to optimize the user-centric neuromodulation therapy preferences through the user feedback. The time series analysis models comprise, but not limited to, at least one of: Recurrent Neural Networks (RNNs), Long Short-Term Memory (LSTM) networks, autoregressive integrated moving average (ARIMA) models, and the like. The time series analysis models are configured to analyze and predict trends in the one or more physiological parameters over time. The natural language processing (NLP) models are configured to process the user-centric data to determine at least one of: the user operational parameter preferences, the therapy goals, and the user feedback for determining the one or more user-centric operational parameters.

In an exemplary embodiment, the operational parameter generation subsystem 210 plays a pivotal role in the system 102 by determining the precise settings for each neuromodulation device 116. The operational parameter generation subsystem 210 is configured to generate the one or more user-centric operational parameters in each neuromodulation device 116 of the one or more neuromodulation devices 116. The generation of the one or more user-centric operational parameters is an up-to-the-minute process that relies on the advanced computational techniques, utilizing using at least one of: the one or more artificial intelligence models and the one or more machine learning models.

The generation of the one or more user-centric operational parameters based on the processed at least one of: the one or more physiological parameters and the user-centric data, for optimizing user-centric neuromodulation therapy preferences. By processing the one or more physiological parameters and the user-centric data, the system 102 is able to tailor the neuromodulation therapy to the user's specific needs and preferences, ensuring that the neuromodulation therapy is both effective and personalized. The operational parameter generation subsystem 210 is responsible for continuously optimizing the one or more user-centric operational parameters, which are essential for controlling the associated neuromodulation device 116.

The one or more user-centric operational parameters directly influence how the neuromodulation device 116 delivers the neuromodulation therapy, including how electrical signals are administered to the body. The one or more user-centric operational parameters that are generated by the operational parameter generation subsystem 210 comprise at least one of: a pulse width, a stimulation amplitude, a stimulation frequency, a simulation intensity, and an impedance, associated with the induced electrical signals, each of which is critical to the effective functioning of the neuromodulation therapy. The pulse width refers to the duration of each electrical pulse delivered by the associated neuromodulation device 116. Adjusting the pulse width allows the system 102 to control the amount of time the nerves or muscles are exposed to each electrical signal, which may influence the therapeutic effect. The stimulation amplitude refers to a strength or intensity of the electrical signals. By optimizing the stimulation amplitude, the system 102 ensures that the electrical signals are strong enough to achieve the desired therapeutic outcome without causing discomfort or adverse effects to the associated user. The frequency refers to the rate at which electrical signals are delivered. The frequency of stimulation is a key factor in determining the type of response elicited from the nervous system or muscles. For example, higher frequencies may be used to block pain signals, while lower frequencies may be used for muscle strengthening. The impedance refers to the resistance encountered by the electrical signals as they pass through the body. Monitoring and adjusting impedance is crucial for ensuring that the electrical signals are delivered effectively and that the therapy remains consistent over time.

The one or more user-centric operational parameters are not static; they are continuously refined and adjusted by the operational parameter generation subsystem 210 based on ongoing feedback from the one or more physiological parameters and user-centric data. This dynamic adjustment process ensures that the neuromodulation therapy remains aligned with the user's evolving physiological state and therapy preferences, providing a highly personalized therapy experience.

In an exemplary embodiment, the data recommendation subsystem 212 is configured to transmit the generated one or more user-centric operational parameters to the associated neuromodulation device 116 of the one or more neuromodulation devices 116. The transmission process is critical for enabling real-time control of the neuromodulation devices 116, ensuring that the neuromodulation therapy administered is precisely tailored to the needs of each user for controlling operations of the one or more neuromodulation devices 116. Once the one or more user-centric operational parameters have been generated-based on the detailed analysis of the one or more physiological parameters and user-centric data, it is the responsibility of the data recommendation subsystem 212 to ensure that these parameters are communicated to the relevant neuromodulation device 116. The data recommendation subsystem 212 functions as the bridge between the data analysis components of the system 102 and the actual therapeutic hardware (one or more neuromodulation devices 116), playing a pivotal role in translating computational insights into actionable therapeutic interventions.

The controlling operations conducted by the neuromodulation devices 116, under the direction of the data recommendation subsystem 212, involve the precise delivery of the electrical signals to targeted areas of the user's body. These electrical signals are induced through the associated neuromodulation device 116, which is configured to administer the neuromodulation therapy according to the specific parameters that have been customized for each user of the one or more users. The controlling operations are not generic but are highly individualized, as they are based on the one or more user-centric operational parameters. These parameters dictate key aspects of the electrical signals, such as pulse width, the stimulation amplitude, the stimulation frequency, the stimulation intensity, and impedance, ensuring that the therapy is optimized for the unique physiological state and therapeutic needs of each user.

The delivery of these electrical signals is targeted at defined treatment areas on the body of the associated user of the one or more users. These treatment areas are carefully selected based on the nature of the condition being treated and the desired therapeutic outcomes. For instance, in the case of chronic pain management, the treatment areas may correspond to specific nerve pathways where pain signals are generated or transmitted. The neuromodulation device 116, guided by the user-centric operational parameters, delivers electrical stimulation directly to these areas, thereby modulating nerve activity in a way that alleviates pain or enhances bodily function.

By continuously controlling the operations of the one or more neuromodulation devices 116 based on real-time data and AI-driven insights, the system 102 is able to provide a highly responsive and adaptive form of neuromodulation therapy. The data recommendation subsystem 212 ensures that the neuromodulation therapy remains aligned with the user's evolving one or more physiological conditions and therapy preferences, thereby maximizing therapeutic efficacy, and improving user satisfaction.

In an exemplary embodiment, the system further comprises the plurality of modules 214 as depicted in FIG. 2B and FIG. 2C. The plurality of modules 214 comprises a learning module 216, a survey module 218, a community module 220, a logging module 222, a provider identification module 224, an educational resource providing module 226, a neuromodulation products recommendation module 228, a remote therapy monitoring (RTM) module 230, a remote patient monitoring (RPM) module 232, an invoice generating module 234, and a dashboard module 236.

In an exemplary embodiment, the learning module 216 is configured with an adaptive learning model that continuously refines and optimizes at least one of: the one or more artificial intelligence models and the one or more machine learning models that are integral to the system's operation. This continuous optimization is achieved through the analysis of real-time data, specifically at least one of: the one or more physiological parameters and the user-centric data. The adaptive learning model within the learning module 216 is configured to constantly analyze the obtain data streams from the one or more users. The one or more physiological parameters provide real-time insights into the user's bodily responses to the neuromodulation therapy, such as changes in heart rate, muscle activity, skin conductivity, and other relevant metrics. Simultaneously, the user-centric data offers a personalized perspective, incorporating the user's preferences, goals, and feedback regarding the therapy. By evaluating this data in real-time, the adaptive learning model identifies patterns, trends, and correlations that inform the ongoing optimization of the one or more artificial intelligence models and the one or more machine learning models.

As the system 102 receives more data over time, the learning module 216 becomes increasingly adept at predicting the one or more user's needs and adjusting the neuromodulation therapy accordingly. This results in a more personalized, effective, and responsive therapy that evolves with the one or more user's changing physiological state and preferences. The continuous learning process ensures that the system 102 remains up-to-date with the latest data, improving its accuracy and effectiveness in delivering targeted neuromodulation therapy.

In an exemplary embodiment, the survey module 218 is configured to provide a pre-defined set of queries to one or more users during at least one of: a pre-treatment phase and a post-treatment phase. These pre-treatment phase and the post-treatment phase are strategically selected to capture the user's baseline conditions before the neuromodulation therapy begins and their responses after the neuromodulation therapy has been administered. During the pre-treatment phase, the survey module 218 may present the pre-defined set of queries configured to establish the user's initial condition, expectations, and specific goals for the neuromodulation therapy. The pre-defined set of queries may include questions about the user's current level of discomfort, their desired outcomes, and any previous experiences with neuromodulation therapy.

In the post-treatment phase, the survey module 218 focuses on collecting feedback regarding the user's experience during and after the neuromodulation therapy. This includes obtaining at least one of, but not limited to, visual analog score (VAS) results, patient global impression of change (PGIC) results, Patient-Reported Outcomes Measurement Information System (PROMIS) score, Oxygen Desaturation Index (ODI), clinical trial data, real-world data, and the like. The VAS results provide a quantitative measure of the user's perceived pain levels, offering a modest yet effective way to gauge the impact of the neuromodulation therapy. The PGIC results capture the user's overall impression of how much their condition has improved or worsened as a result of the neuromodulation therapy, providing a broader assessment of therapeutic efficacy. The clinical trial data may include specific metrics or observations recorded during the neuromodulation therapy, which contribute to a deeper understanding of the therapy's effectiveness and safety. The data collected by the survey module 218 is crucial to continuously update and optimize at least one of: the one or more artificial intelligence models and the one or more machine learning models In an exemplary embodiment, the community module 220 is configured to connect the one or more users receiving the neuromodulation therapy to a network of cohort users. The community module 220 establishes an engaging environment for the one or more users through the user application 106a for sharing at least one of: experiences, progress, and feedback, fostering a collaborative environment. The community module 220 utilizes user profile credentials and display names to facilitate features like personal timelines, newsfeeds, timelines, comments, follow/tag/likes, private messaging, group interactions, live video streaming, stories, customer support, and sponsored posts. The learning module 216 collaborates with community module 220 to predict adjustments to therapies based on community interactions and shared experiences.

In an exemplary embodiment, the logging module 222 is configured to generate log data for each user of the one or more users based on the user-centric neuromodulation therapy preferences. The logging module 222 is configured to acquire, curate, and generate log data related to therapeutic programs. The log data comprises at least one of: a therapy duration, therapy timelines, and the one or more user-centric operational parameters. The logging module 222 is configured to capture details such as duration, efficacy, and frequency of the neuromodulation therapy. The logging module 222 collaborates with the survey module 218 to enrich the dataset with insights from the feedback, contributing to the continuous learning process of the learning module 216.

In an exemplary embodiment, the provider identification module 224 is configured to connect the one or more users with the one or more healthcare providers based on one or more attributes. The one or more attributes comprise, but not limited to, at least one of: location, proficiency in the neuromodulation therapy, acquaintance with the one or more neuromodulation devices, and the like. The provider identification module 224 ensures that the one or more users are connected with relevant one or more healthcare providers for support and guidance. The provider identification module 224 enhances the overall user experience and facilitates a seamless connection between the one or more users and the one or more healthcare providers.

In an exemplary embodiment, the educational resource providing module 226 is configured to provide one or more educational resources to at least one of: the one or more users and the one or more healthcare providers. The one or more educational resources comprise, but not limited to, at least one of: instructional videos, neuromodulation therapy documentations, and one or more manuals related to at least one of: the neuromodulation therapy and the one or more neuromodulation devices 116. The educational resource providing module 226 may include instructional videos for the one or more neuromodulation devices 116 installation or adjustments. The one or more users, including experts such as physicians, technicians, patients, and the associated users, may generate the one or more educational resources. The educational resource providing module 226 contributes to individual empowerment by enhancing understanding and knowledge about the neuromodulation therapy.

In an exemplary embodiment, the neuromodulation products recommendation module 228 is configured to depict at least one of: one or more advertisements and sponsored content on the one or more communication devices 106 associated with each user of one or more users. The at least one of: one or more advertisements and sponsored content is configured to provide product suggestions related to the neuromodulation therapy. The neuromodulation products recommendation module 228 ensures that sponsored posts are strategically placed, offering relevant resources and information to the one or more users. The neuromodulation products recommendation module 228 contributes to the commercial aspect of the application while maintaining user-centricity.

The RTM module 230 is configured to monitor the real-time efficacy of the neuromodulation therapy by analyzing the obtained user-centric data for generating the one or more user-centric operational parameters. The RTM module 230 focuses on support monitoring functions associated with the one or more neuromodulation devices 116. The RTM module 230 generates data, extracts insights, and determines the efficacy of RTM-based device implementations. The RTM module 230 correlates the stimulation frequency, the stimulation amplitude, pulse width programming, and user therapy programs with improvements in visual analog pain score and patient global impression of change score. In one embodiment, the RTM module 230 is configured with 30 programs (as depicted in Table 1) that constitute various clinical functions around relief, strengthening, and relaxation of muscles but are not limited to these therapeutic paradigms.

TABLE 1

| Cat. in the APP | Program under the category in the APP | Mode | Treatment Time (min) | Output Voltage (Vrms) | Pulse Durations (µs) | Pulse Repetition Frequencies (Hz) |
|---|---|---|---|---|---|---|
| Relieve | General Pain Relief (Default Program before Any Change) | TENS | 20 | 10.0 | 4-150 | 150-304 |
| | Advanced Pain Relief | TENS | 20 | 7.5 | 4-150 | 85-130 |
| | Mixed Frequency | TENS | 20 | 6.5 | 50 | 50-180 |
| | Deep Stimulus-Basic | TENS | 20 | 7.2 | 150 | 80 |
| | Deep Stimulus-Advanced | TENS | 20 | 4.6 | 30 | 100 |
| | Pain Block | TENS | 20 | 2.7 | 250 | 5 |
| | Thorough Stimulus-Mild | TENS | 60 | 7.2 | 150 | 80 |
| | Thorough Stimulus-Moderate | TENS | 60 | 8.0 | 200 | 100 |
| | Thorough Stimulus-Advanced | TENS | 60 | 7.7 | 71-200 | 100 |
| | Pain Relief Massage-Pounding | TENS | 30 | 1.5 | 200 | 2 |
| | Pain Relief Massage-combination of rubbing and pounding | TENS | 30 | 7.7 | 150 | 2-100 |
| | Back of Neck Pain Relief | TENS | 20 | 2.7 | 250 | 5 |
| | Back Pain Relief | TENS | 20 | 3.0 | 300 | 5 |
| | Deep Burst-Basic | TENS | 15 | 3.3 | 100 | 1-15 |
| | Deep Burst-Advanced | TENS | 20 | 7.8 | 4-100 | 920-1200 |
| | Complete Massage | TENS | 20 | 3.6 | 4-100 | 1-19 |
| Strengthen | Muscle Strengthening-Basic | EMS | 32 | 7.7 | 250 | 3-75 |
| | Muscle Strengthening-Intermediate | EMS | 32 | 8.1 | 250 | 3-100 |
| | Muscle Strengthening-Advanced | EMS | 32 | 7.8 | 250 | 3-87 |
| | Improve Muscle Performance & Endurance-Basic | EMS | 45 | 3.9 | 250 | 3-10 |
| | Improve Muscle Performance & Endurance-Intermediate | EMS | 45 | 4.3 | 250 | 3-15 |
| | Improve Muscle Performance & Endurance-Advanced | EMS | 45 | 5.2 | 250 | 3-20 |
| | Muscle Stimulation Flux-Basic | EMS | 35 | 6.5 | 250 | 3-35 |
| | Muscle Stimulation Flux-Advanced | EMS | 35 | 6.9 | 250 | 3-45 |
| Relax | Lower Leg Muscle Stimulation Flow-Basic | EMS | 15 | 4.2 | 400 | 2-8 |
| | Lower Leg Muscle Stimulation Flow-Advanced | EMS | 20 | 8.3 | 400 | 5-60 |
| | Sore Muscle Massage | EMS | 30 | 6.7 | 250 | 3-40 |
| | Muscle Stimulation Bounce | EMS | 30 | 1.4 | 250 | 1 |
| | Muscle Stimulation Pulse | EMS | 35 | 3.7 | 400 | 3-7 |

TABLE 1-continued

| Cat. in the APP | Program under the category in the APP | Mode | Treatment Time (min) | Output Voltage (Vrms) | Pulse Durations (µs) | Pulse Repetition Frequencies (Hz) |
|---|---|---|---|---|---|---|
| | Muscle Stimulation Wave | EMS | 28 | 3.4 | 250 | 1-8 |

In an exemplary embodiment, the RPM module 232 is configured to analyze obtained at least one of: the one or more physiological parameters and the user-centric data in real-time. The analysis is configured to alter the one or more user-centric operational parameters in the associated neuromodulation device 116. The RPM module 232 is configured support monitoring functions associated with the one or more neuromodulation devices 116. The RPM module 232 collects data related to the stimulation frequency, the stimulation amplitude, the pulse width programming, and individual therapy programs. This data correlates with pain intensity and the overall well-being of the associated user. The RPM Module 232 aligns with billing guidelines for RPM and RTM codes.

In an exemplary embodiment, the invoice generating module 234 is configured to generate invoice or super bills for clinics based on the data generated by the RPM module 232 and RTM module 230. The invoice generating module 234 automates the invoice/billing process, formatting invoice/bills for submission according to Centers for Medicare & Medicaid Services (CMS) guidelines. The invoice generating module 234 ensures accuracy and efficiency in billing practices. The invoice generating module 234 includes interpretation mechanisms that automate the provision of billing communication modalities. Leveraging natural language processing techniques, the interpretation mechanism facilitate the automatic generation of billing communications in a clear and comprehensible natural language format. This streamlines the communication between the system 102 and the one or more users, ensuring transparency in invoice/billing procedures.

The invoice generating module 234 is configured to generate invoices in strict adherence to various billing standard requirements and CPT (Current Procedural Terminology) code specifications. By ensuring compliance with established invoice/billing standards, The invoice generating module 234 contributes to the accuracy and integrity of the invoice/billing process. The invoice generating module 234 seamlessly integrates with clinical Electronic Medical Record (EMR) systems of individual practices, regardless of their size. This integration automates the invoice/billing process, eliminating manual interventions and reducing the likelihood of errors. The invoice generating module 234 extracts relevant data from the EMR to generate bills with precision.

To optimize workflow and enhance user experience, The invoice generating module 234 formats invoices in a dashboard and application (APP) interface. This application (APP) interface is configured to be both physician and patient-centric, providing a user-friendly platform for accessing billing information. The dashboard offers a visual representation of invoice data, facilitating informed decision-making for both the one or more healthcare providers and the one or more users.

In an exemplary embodiment, the dashboard module 236 is operatively connected to the one or more communication devices. The dashboard module 236 is configured to display visual representations related to at least one of: the neuromodulation therapy outcomes, the real-time one or more physiological parameters, the one or more user-centric operational parameters, and the invoice data. The visual representations are configured to provide information to at least one of: the one or more users and the one or more healthcare providers regarding the neuromodulation therapy.

In an exemplary embodiment, the flowchart 200C as depicted in FIG. 2C, involves initiating with the data obtaining subsystem 206 obtaining at least one of: the one or more physiological parameters from the one or more neuromodulation devices 116 and the user-centric data from the one or more communication devices 106 associated with each user of one or more users. Subsequently, the data-processing subsystem 208 is configured to process the obtained at least one of: the one or more physiological parameters and the user-centric data using at least one of: the one or more artificial intelligence models and the one or more machine learning models. The at least one of the: artificial intelligence model and machine learning model decipher complex patterns, correlations, and trends within the data, and creating a comprehensive understanding of the associated user's physiological responses. The operational parameter generation subsystem 210 generates the one or more user-centric operational parameters for optimizing the neuromodulation therapy based on the output data from the at least one of the: artificial intelligence model and machine learning model. These recommendations, encompassing adjustments to the pulse width, the stimulation amplitude, the stimulation frequency, the stimulation intensity, and impedance, ensure a tailored approach aligned with the individual's therapeutic needs. Simultaneously, the analytics subsystem facilitates continuous learning of the at least one of the: artificial intelligence model and machine learning model, allowing the system 102 to adapt to new data and evolving user preferences over time.

The system 102 incorporates the plurality of modules 214 configured for specific functionalities, such as machine learning operations, survey data acquisition, community engagement, therapy program logging, provider identification, education content delivery, commercial interactions, remote therapy monitoring, remote patient monitoring, billing automation, and dashboard presentation, respectively. This comprehensive flow chart 200C ensures a holistic and adaptive approach to neuromodulation therapy based on real-time physiological parameters and user interactions.

Figure 3:
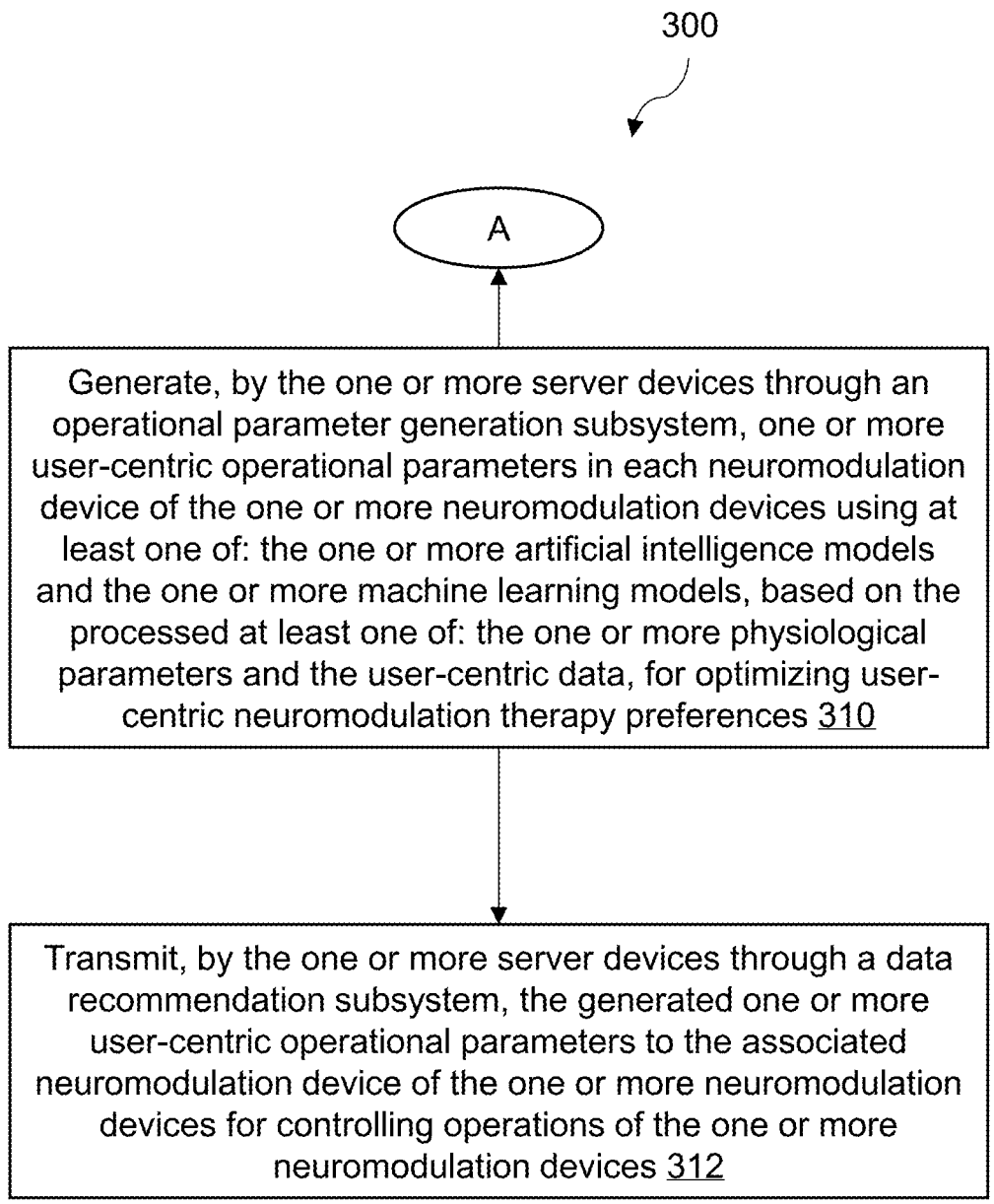
FIG. 3 illustrates an exemplary flow chart of an AI-based method for controlling the operations of the one or more neuromodulation devices based on the one or more physiological parameters of the one or more users, in accordance with an embodiment of the present disclosure.
Figure 3:
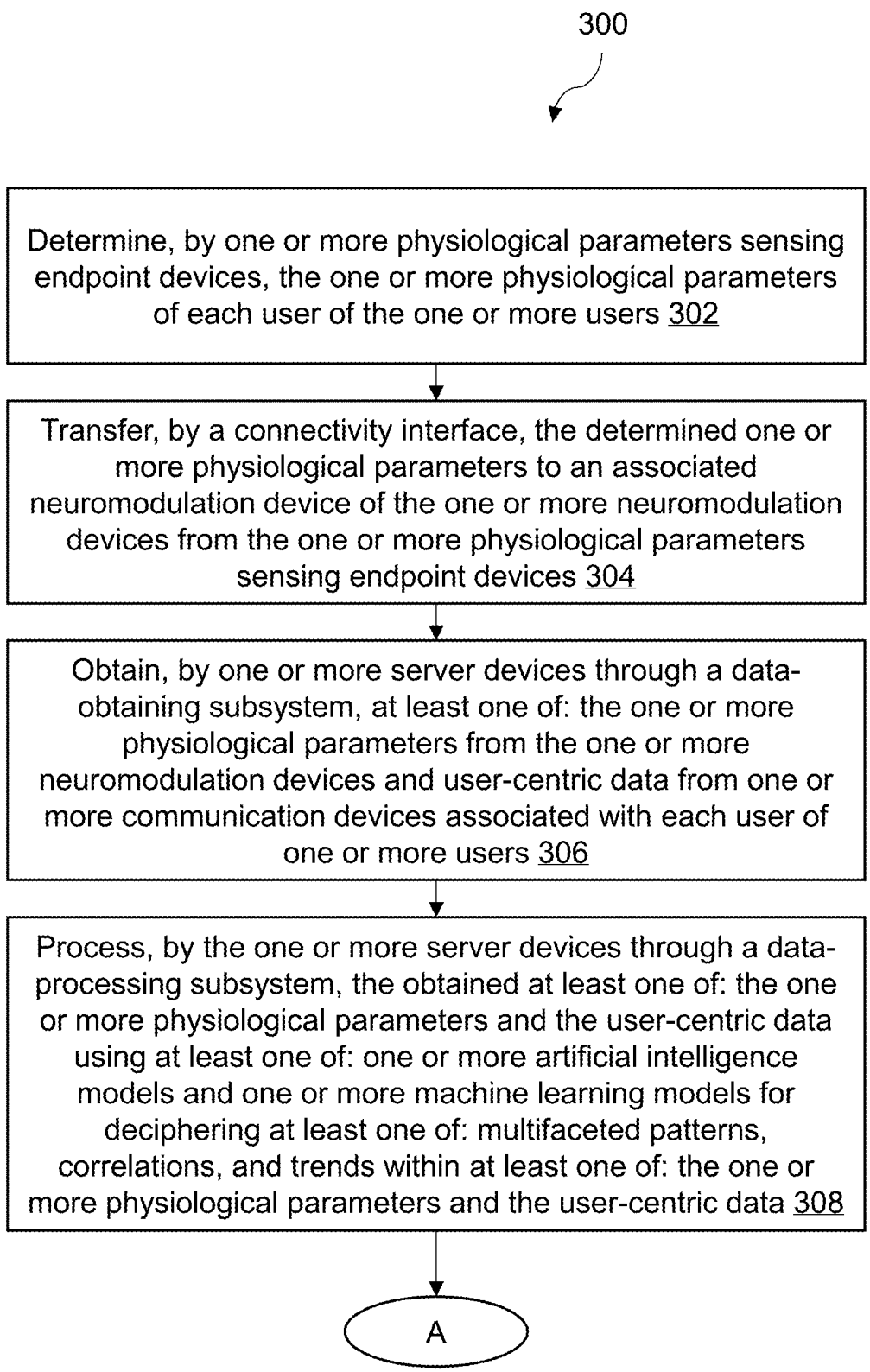

FIG. 3 illustrates an exemplary flow chart of an AI-based method 300 for controlling the operations of the one or more neuromodulation devices based on the one or more physiological parameters of the one or more users, in accordance with an embodiment of the present disclosure.

According to another exemplary embodiment of the present disclosure, the AI-based method 300 for controlling the operations of the one or more neuromodulation devices 116 based on the one or more physiological parameters of the one or more users is disclosed. The one or more physiological parameters comprise at least one of: heart rate, muscle activity, skin conductivity, blood oxygen levels (SpO2), blood pressure, temperature, respiratory rate, electrical impedance, nerve activity, and user posture and movement. At step 302, the AI-based method 300 includes determining, by the one or more physiological parameters sensing endpoint devices, the one or more physiological parameters of each user of the one or more users. At step 304, the AI-based method 300 includes transferring, by the connectivity interface, the determined the one or more physiological parameters to the associated neuromodulation device of the one or more neuromodulation devices from the one or more physiological parameters sensing endpoint devices.

At step 306, the AI-based method 300 includes obtaining, by the one or more server devices through the data-obtaining subsystem, at least one of: the one or more physiological parameters from the one or more neuromodulation devices and the user-centric data from the one or more communication devices associated with each user of one or more users. At step 308, the AI-based method 300 includes processing, by the one or more server devices through the data-processing subsystem, the obtained at least one of: the one or more physiological parameters and the user-centric data using at least one of: the one or more artificial intelligence models and the one or more machine learning models for deciphering at least one of: multifaceted patterns, correlations, and trends within at least one of: the one or more physiological parameters and the user-centric data. The at least one of: the one or more artificial intelligence models and the one or more machine learning models comprises at least one of: the supervised learning models, the unsupervised learning models, the reinforcement learning models, the time series analysis models, and the natural language processing (NLP) models.

At step 310, the AI-based method 300 includes generating, by the one or more server devices through the operational parameter generation subsystem, the one or more user-centric operational parameters in each neuromodulation device of the one or more neuromodulation devices using at least one of: the one or more artificial intelligence models and the one or more machine learning models, based on the processed at least one of: the one or more physiological parameters and the user-centric data, for optimizing the user-centric neuromodulation therapy preferences. At step 312, the AI-based method 300 includes transmitting, by the one or more server devices through the data recommendation subsystem, the generated one or more user-centric operational parameters to the associated neuromodulation device of the one or more neuromodulation devices for controlling operations of the one or more neuromodulation devices. The controlling operations comprise inducing the electrical signals through the associated neuromodulation device of the one or more neuromodulation devices, on the defined treatment areas on the body of the associated user of the one or more users based on the one or more user-centric operational parameters.

Further, in the next step, the AI-based method 300 includes optimizing, by the learning module configured with the adaptive learning model, at least one of: the one or more artificial intelligence models and the one or more machine learning models based on analyzing real-time at least one of: the one or more physiological parameters and the user-centric data. In the next step, the AI-based method 300 includes providing, by the survey module, the pre-defined set of queries to one or more users during at least one of: the pre-treatment phase and the post-treatment phase to obtain at least one of: the visual analog score (VAS) results, the patient global impression of change (PGIC) results, and the clinical trial data, to continuously update and optimize at least one of: the one or more artificial intelligence models and the one or more machine learning models.

In the next step, the AI-based method 300 includes connecting, by the community module, the one or more users receiving the neuromodulation therapy to the network of cohort users for sharing at least one of the: experiences, progress, and feedback, fostering a collaborative environment through at least one of: comments, follows, likes, and group interactions. In the next step, the AI-based method 300 includes generating, by the logging module, log data for each user of the one or more users based on the user-centric neuromodulation therapy preferences, wherein the log data comprises at least one of: the therapy duration, therapy timelines, and the one or more user-centric operational parameters.

In the next step, the AI-based method 300 includes connecting, by the provider identification module, the one or more users with the one or more healthcare providers based on the one or more attributes comprise at least one of: the location, the proficiency in the neuromodulation therapy, and the acquaintance with the one or more neuromodulation devices. In the next step, the AI-based method 300 includes providing, by the educational resource providing module, the one or more educational resources to at least one of: the one or more users and the one or more healthcare providers. The one or more educational resources comprise at least one of: the instructional videos, the neuromodulation therapy documentations, and the one or more manuals related to at least one of: the neuromodulation therapy and the one or more neuromodulation devices.

In the next step, the AI-based method 300 includes depicting, by the neuromodulation products recommendation module, at least one of: the one or more advertisements and the sponsored content to the one or more communication devices associated with each user of one or more users, to provide product suggestions related to neuromodulation therapy. In the next step, the AI-based method 300 includes monitoring, by the RTM module, the real-time efficacy of the neuromodulation therapy by analyzing the obtained user-centric data to generate the one or more user-centric operational parameters. In the next step, the AI-based method 300 includes analyzing, by the RPM module, obtained at least one of: the one or more physiological parameters and the user-centric data in real-time to alter the one or more user-centric operational parameters in the associated neuromodulation device. In the next step, the AI-based method 300 includes displaying, by the dashboard module, visual representations related to at least one of: the neuromodulation therapy outcomes, the real-time one or more physiological parameters, the one or more user-centric operational parameters, and the invoice data generated in the invoice generation subsystem, to provide information to at least one of: the one or more users and the one or more healthcare providers regarding the neuromodulation therapy.

Figure 4:
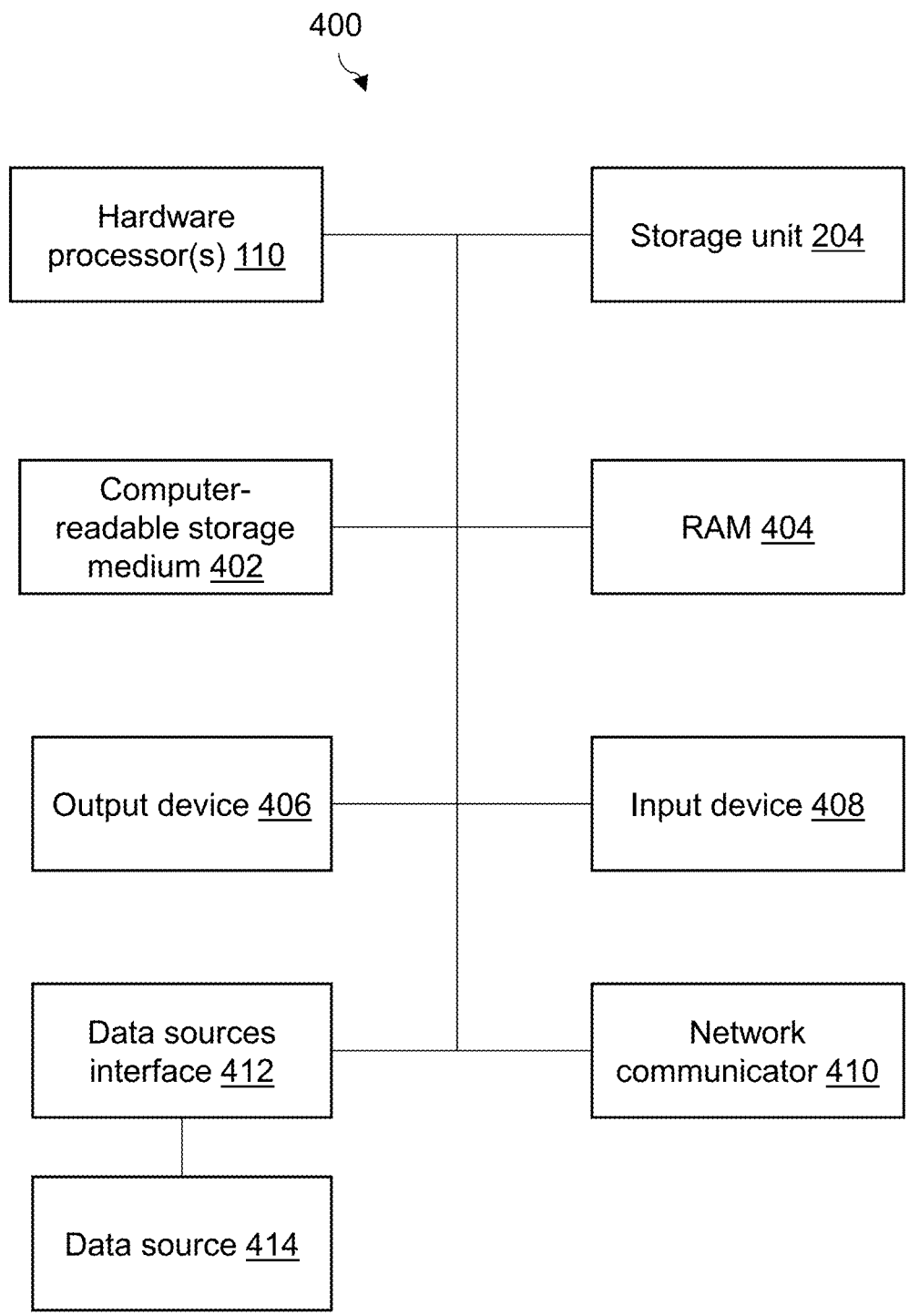
FIG. 4 illustrates an exemplary block diagram representation of a server platform for implementation of the disclosed AI-based system, in accordance with an embodiment of the present disclosure.

FIG. 4 illustrates an exemplary block diagram representation of one or more server platforms 400 for implementation of the disclosed AI-based system 102, in accordance with an embodiment of the present disclosure.

In an exemplary embodiment, for the sake of brevity, the construction, and operational features of the system 102 which are explained in detail above are not explained in detail herein. Particularly, computing machines such as but not limited to internal/external server clusters, quantum computers, desktops, laptops, smartphones, tablets, and wearables may be used to execute the system 102 or may include the structure of the one or more server platforms 400. As illustrated, the one or more server platforms 400 may include additional components not shown, and some of the components described may be removed and/or modified. For example, a computer system with the multiple graphics processing units (GPUs) may be located on at least one of: internal printed circuit boards (PCBs) and external-cloud platforms including Amazon® Web Services, internal corporate cloud computing clusters, or organizational computing resources.

The one or more server platforms 400 may be a computer system such as the system 102 that may be used with the embodiments described herein. The computer system may represent a computational platform that includes components that may be in the one or more server devices 118 or another computer system. The computer system may be executed by the one or more hardware processors 110 (e.g., single, or multiple processors) or other hardware processing circuits, the methods, functions, and other processes described herein. These methods, functions, and other processes may be embodied as machine-readable instructions stored on a computer-readable medium, which may be non-transitory, such as hardware storage devices (e.g., RAM (random access memory), ROM (read-only memory), EPROM (erasable, programmable ROM), EEPROM (electrically erasable, programmable ROM), hard drives, and flash memory). The computer system may include the one or more hardware processors 110 that execute software instructions or code stored on a non-transitory computer-readable storage medium 402 to perform methods of the present disclosure. The software code includes, for example, instructions to gather data and analyze the network environment data. For example, the plurality of subsystems 114 includes the data-obtaining subsystem 206, the data-processing subsystem 208, the operational parameter generation subsystem 210, and the data recommendation subsystem 212.

The instructions on the computer-readable storage medium 402 are read and stored the instructions in the storage unit or random-access memory (RAM) 404. The storage unit 204 may provide a space for keeping static data where at least some instructions could be stored for later execution. The stored instructions may be further compiled to generate other representations of the instructions and dynamically stored in the RAM 404. The one or more hardware processors 110 may read instructions from the RAM 404 and perform actions as instructed.

The computer system may further include an output device 406 to provide at least some of the results of the execution as output including, but not limited to, visual information to the one or more users, such as the administrators. The output device 406 may include a display on computing devices and virtual reality glasses. For example, the display may be a mobile phone screen or a laptop screen. GUIs and/or text may be presented as an output on the display screen. The computer system may further include an input device 408 to provide the one or more users or another device with mechanisms for entering data and/or otherwise interacting with the computer system. The input device 408 may include, for example, a keyboard, a keypad, a mouse, or a touchscreen. The output device 406 and the input device 408 may be joined by one or more additional peripherals.

A network communicator 410 may be provided to connect the computer system to a network and in turn to other devices connected to the network including other entities, servers, data stores, and interfaces. The network communicator 410 may include, for example, a network adapter such as a LAN adapter or a wireless adapter. The computer system may include a data sources interface 412 to access a data source 414. The data source 414 may be an information resource about the neuromodulation therapy. As an example, the database 104 of exceptions and rules may be provided as the data source 414. Moreover, knowledge repositories and curated data may be other examples of the data source 414. The data source 414 may include libraries containing, but not limited to, datasets related to neuromodulation therapy protocols, patient outcomes, and device-specific operational guidelines. Moreover, the data sources interface 412 enables the system 102 to dynamically access and update these data repositories as latest information is collected, analyzed, and utilized.

Figure 5A:
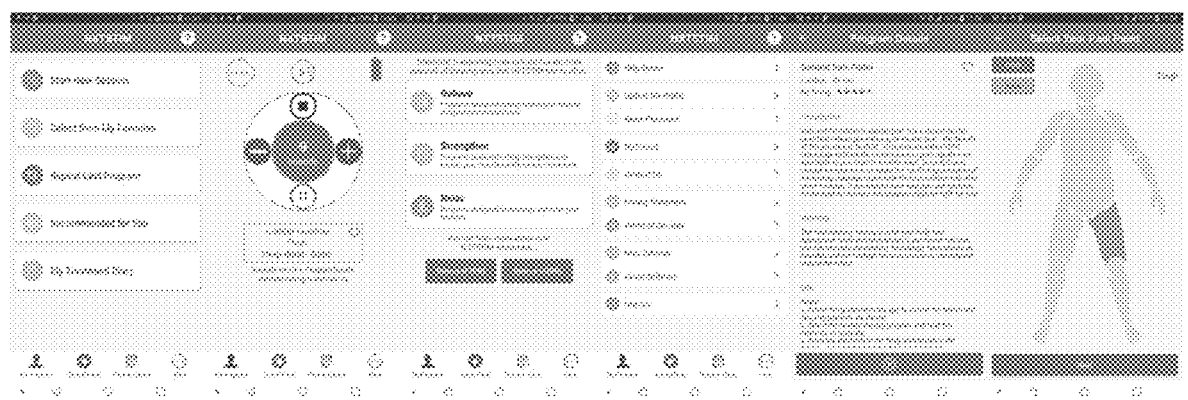
FIG. 5A illustrates an exemplary user interface representation of the AI-based system during one or more experimental trials assisting one or more users to position the one or more neuromodulation device, in accordance with an embodiment of the present disclosure.

FIG. 5A illustrates an exemplary user interface representation of the AI-based system 102 during the one or more experimental trials assisting the one or more users to position the neuromodulation device 500A, in accordance with an embodiment of the present disclosure.

Figure 5B:
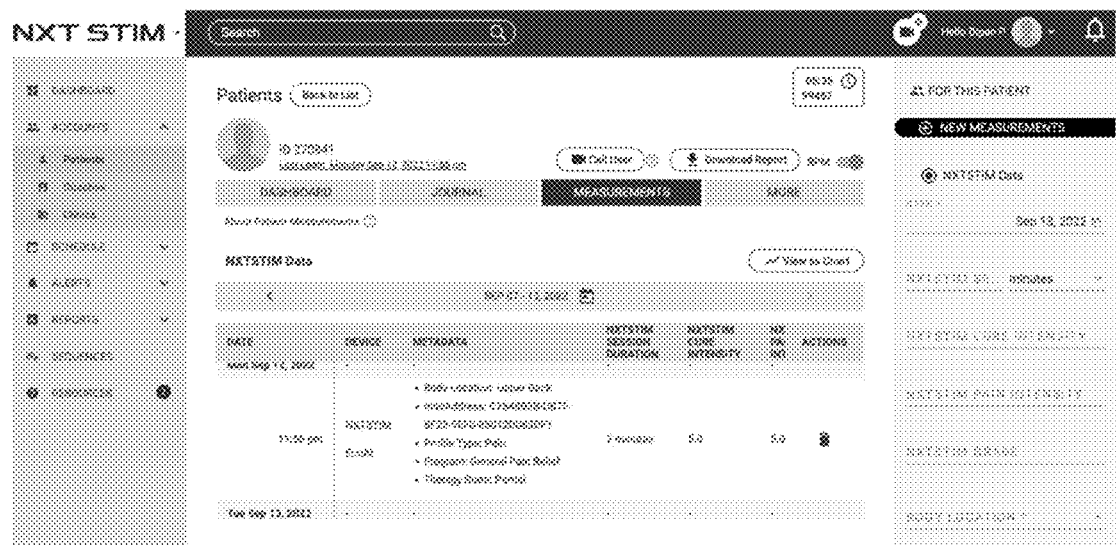
FIG. 5B illustrates an exemplary user interface representation of the AI-based system depicting details of the one or more uses, in accordance with an embodiment of the present disclosure.

FIG. 5B illustrates an exemplary user interface representation of the AI-based system 102 depicting details 500B of the one or more uses, in accordance with an embodiment of the present disclosure.

Figure 5C:
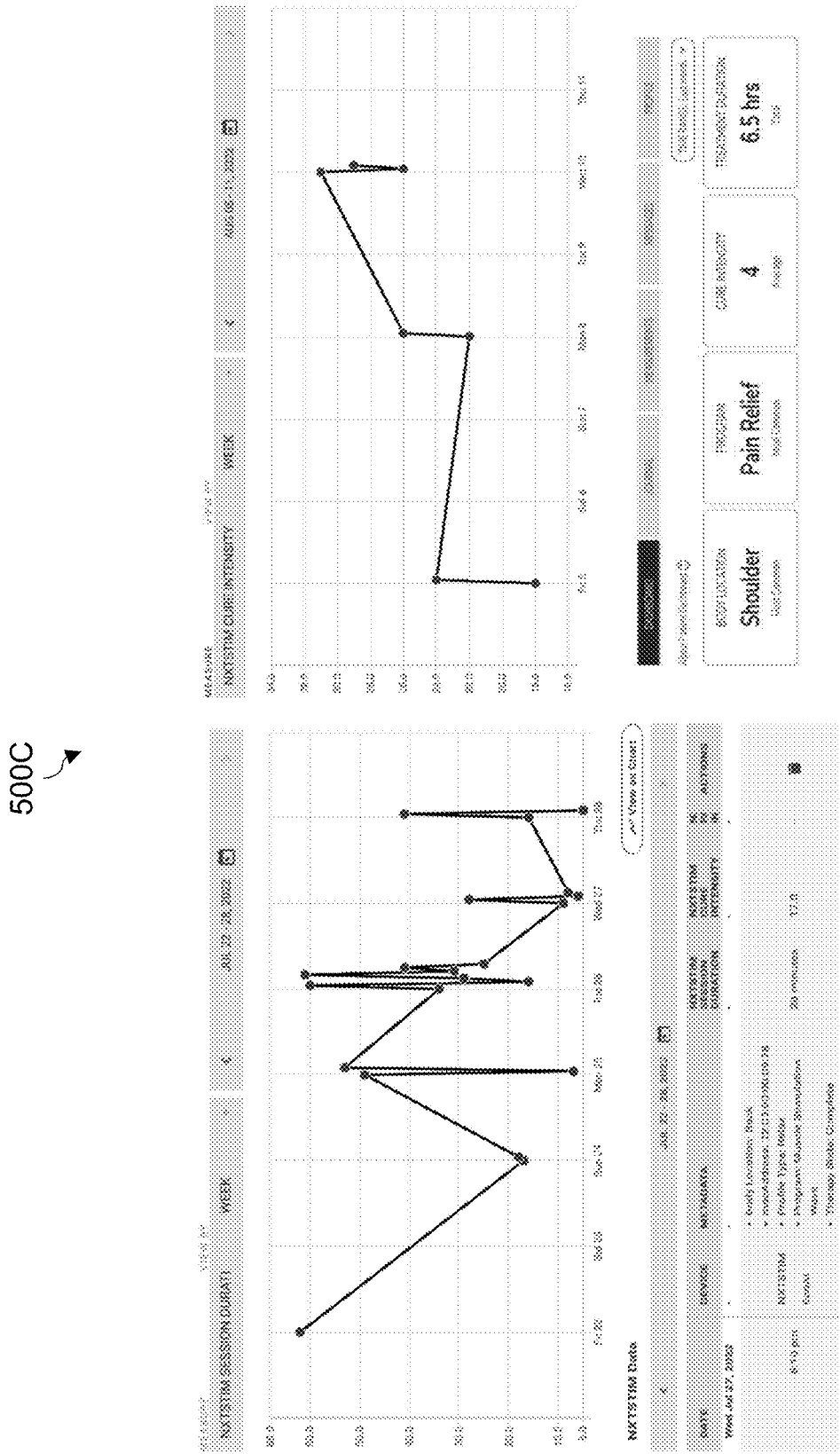
FIG. 5C illustrates an exemplary user interface representation of the AI-based system depicting evolution graphs of a neuromodulation therapy, in accordance with an embodiment of the present disclosure.

FIG. 5C illustrates an exemplary user interface representation of the AI-based system 102 depicting evolution graphs 500C of the neuromodulation therapy, in accordance with an embodiment of the present disclosure.

In an exemplary embodiment, the one or more experimental trials are a six-month retrospective review of prospective, open-label, multi-center registry data, the one or more users suffer with chronic pain conditions (nociceptive, neuropathic, or myofascial) related to the neck, shoulder, or back. The AI-based system is configured to collect the at least one of: the one or more physiological parameters and the user-centric data through the AI-based system application and dashboard from Jun. 1, 2022, to Dec. 31, 2022. The pain scores are monitored weekly using the Visual Analog Scale (VAS), with full surveys conducted at three-month intervals. The one or more experimental trials included the one or more users over 18 years old who had experienced pain for over six months. Out of 545 participants, 363 opted for weekly assessments through the system application.

The outcomes of the one or more experimental trials from the one or more users are 88% (319 out of 363) reported at least a 40% reduction in pain. Over the six-month period, the one or more users logged a total of 5 million minutes (90,000 hours) of the neuromodulation device usage, equivalent to over 250,000 individual user treatments. No adverse events are reported, demonstrating the safety of the neuromodulation device over a substantial number of treatments with average daily usage of around 20 minutes per session.

Figure 6:
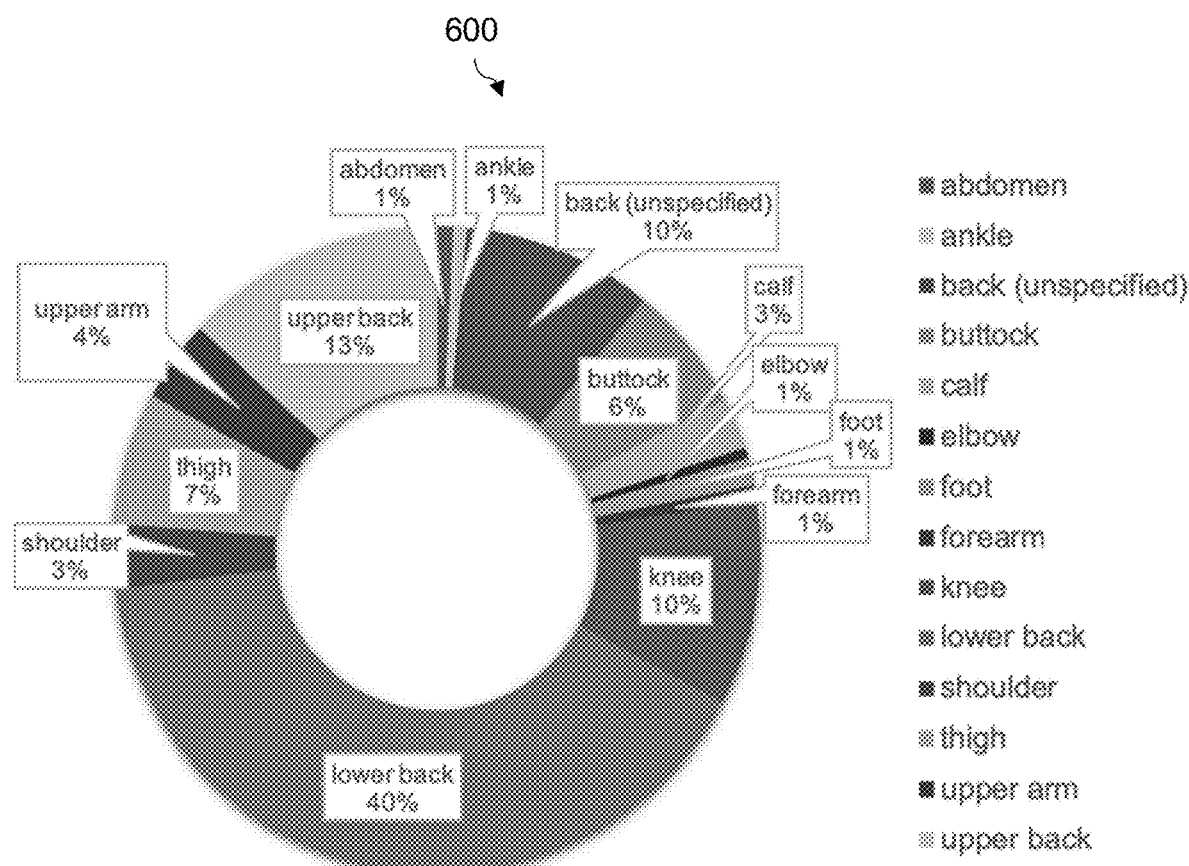
FIG. 6 illustrates an exemplary pie chart representation of one or more experimental trials of the AI-based system at various sites of the one or more users of a neuromodulation therapy, in accordance with an embodiment of the present disclosure.

FIG. 6 illustrates an exemplary pie chart representation 600 of the one or more experimental trials of AI-based system 102 at various sites of the one or more users of a neuromodulation therapy, in accordance with an embodiment of the present disclosure.

In an exemplary embodiment, the AI-based system undergoes the one or more experimental trials. The AI-based system integrates at least one of: the one or more artificial intelligence models and the one or more machine learning models with the transcutaneous electrical nerve stimulation (TENS) and the electromyographic stimulation (EMS) for chronic pain management. The TENS and EMS are non-pharmacologic, non-invasive treatments for managing chronic pain and promoting muscle recovery. The TENS and the EMS are not consistently shown efficacy in traditional trials, which often lack adequate tracking or assessment methods. The one or more neuromodulation devices operates with the AI-based system in a closed-loop, offering personalized pain tracking, remote patient monitoring, and automated treatment adjustments using at least one of: the one or more artificial intelligence models and the one or more machine learning models. This advanced technology aims to overcome the limitations of previous studies by providing real-time data and adaptive therapy. The one or more experimental trials retrospective, analyzing real-world data from the one or more users over an 18-month period (Jan. 1, 2022-Jul. 20, 2024).

The one or more users are at least 18 years old, had chronic nociceptive, neuropathic, or myofascial pain for at least six months, and agreed to provide weekly visual analog scale (VAS) scores for pain assessment. The AI-based system is configured to collect the at least one of: the one or more physiological parameters and the user-centric data. The one or more users are identified as those who experienced at least a 40% improvement in VAS scores from baseline.

A total of 550 users provided weekly VAS scores. Back pain is the most common reason for the neuromodulation therapy, with 40% reporting use for lower back pain, 13% for upper back pain, and 10% for unspecified back pain. Other areas treated included the knee (10%) and neck (7%). On average, daily usage time of the neuromodulation device is 23 minutes, with an intensity average of 39.72V. At the 18-month mark, 484 out of 550 participants (88%) reported at least a 20% reduction in pain, 363 participants (66%) achieved a 40% or greater reduction in pain, indicating a strong response to the neuromodulation therapy using the neuromodulation device configured with the AI-based system. The results depicted in Table 2

TABLE 2

| Parameters | N(%) at 18 months |
| --- | --- |
| Number of users | 1452 |
| Number of users opt for weekly assessments | 550 (38% of 1452 total) |
| Number of users who reported ≥20% reduced pain | 484 (88% of 550) |
| Number of users who reported ≥40% reduced pain | 363 (66% of 550) |

No adverse events are reported, suggesting that the neuromodulation device is safe for long-term use by the one or more users. The one or more experimental trials underscores the potential of large datasets and AI for personalizing and optimizing chronic pain treatment. The AI-based system with close-loop facilitated real-time pain monitoring and dynamic therapy adjustments, enhancing patient outcomes.

Numerous advantages of the present disclosure may be apparent from the discussion above. In accordance with the present disclosure, the system for controlling the operations of one or more neuromodulation devices based on the one or more physiological parameters of one or more users. The one or more users undergoing neuromodulation therapy experience a highly personalized and adaptive approach to their treatment. The system's ability to continuously monitor real-time physiologic parameters, coupled with the integration of machine learning and artificial intelligence models, ensures that therapeutic recommendations are dynamically adjusted based on the individual's unique responses. The system not only optimizes the effectiveness of neuromodulation therapy but also enhances the overall user experience by providing tailored and responsive interventions.

Moreover, the incorporation of the community module fosters a sense of support and collaboration among the users sharing similar therapeutic journeys. The client application's rich features, including personal timelines, newsfeeds, private messaging, and community interactions, create a vibrant environment for users to connect, share insights, and receive mutual support. The continuous learning facilitated by the learning module, and survey module ensures that the system evolves over time, gaining insights from both individual experiences and community interactions.

A description of an embodiment with several components in communication with each other does not imply that all such components are required. On the contrary, a variety of optional components are described to illustrate the wide variety of possible embodiments of the invention. When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of the more than one device or article, or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open-ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

What is claimed is:

1. An artificial intelligence (AI)-based system for controlling operations of one or more neuromodulation devices based on one or more physiological parameters of one or more users, comprising:

one or more physiological parameters sensing endpoint devices operatively connected to each neuromodulation device of the one or more neuromodulation devices, configured to determine the one or more physiological parameters of each user of the one or more users;

a connectivity interface configured in each neuromodulation device of the one or more neuromodulation devices to operatively connect with each physiological parameters sensing endpoint device of the one or more physiological parameters sensing endpoint devices for transferring the determined one or more physiological parameters to an associated neuromodulation device of the one or more neuromodulation devices; and one or more server devices configured with one or more server applications operatively connected to the one or more neuromodulation devices, the one or more server devices comprising:

one or more hardware processors; and a memory unit operatively connected to the one or more hardware processors, wherein the memory unit comprises a set of computer-readable instructions in form of a plurality of subsystems, configured to be executed by the one or more hardware processors, wherein the plurality of subsystems comprises:

a data-obtaining subsystem configured to obtain at least one of: the one or more physiological parameters from the one or more neuromodulation devices and user-centric data from one or more communication devices associated with each user of one or more users;

a data-processing subsystem configured to process the obtained at least one of: the one or more physiological parameters and the user-centric data using at least one of: one or more artificial intelligence models and one or more machine learning models for deciphering at least one of: multifaceted patterns, correlations, and trends within at least one of: the one or more physiological parameters and the user-centric data;

an operational parameter generation subsystem configured to generate one or more user-centric operational parameters in each neuromodulation device of the one or more neuromodulation devices using at least one of: the one or more artificial intelligence models and the one or more machine learning models, based on the processed at least one of: the one or more physiological parameters and the user-centric data, for optimizing user-centric neuromodulation therapy preferences;

a data recommendation subsystem configured to transmit the generated one or more user-centric operational parameters to the associated neuromodulation device of the one or more neuromodulation devices for controlling operations of the one or more neuromodulation devices;

a learning module configured with an adaptive learning model to continuously optimize at least one of: the one or more artificial intelligence models and the one or more machine learning models based on analyzing real-time at least one of: the one or more physiological parameters and the user-centric data;

a survey module configured to provide a pre-defined set of queries to one or more users during at least one of: a pre-treatment phase and a post-treatment phase for obtaining at least one of: visual analog score (VAS) results, patient global impression of change (PGIC) results, Patient-Reported Outcomes Measurement Information System (PROMIS) score, Oxygen Desaturation Index (ODI), clinical trial data, and real-world data, to continuously update and optimize at least one of: the one or more artificial intelligence models and the one or more machine learning models;

a remote therapy monitoring (RTM) module configured to monitor the real-time efficacy of the neuromodulation therapy by analyzing the obtained user-centric data for generating the one or more user-centric operational parameters; and a remote patient monitoring (RPM) module configured to analyze obtained at least one of: the one or more physiological parameters and the user-centric data in real-time for altering the one or more user-centric operational parameters in the associated neuromodulation device, wherein the controlling operations comprise inducing electrical signals through the associated neuromodulation device of the one or more neuromodulation devices, on defined treatment areas on a body of an associated user of the one or more users based on the one or more user-centric operational parameters.

2. The artificial intelligence (AI)-based system of claim 1, wherein each neuromodulation device of the one or more neuromodulation devices comprises one or more electrode pads for inducing the electrical signals onto the defined treatment areas, one or more electrode pads are configured to deliver the electrical signals as neuromodulation waveforms with frequencies ranging between 0.000001 hertz (Hz) to 100,000 hertz (Hz);

each neuromodulation device of the one or more neuromodulation devices comprises at least one of: an electrocardiogram (ECG) sensor, an electromyography (EMG) sensor, a skin conductivity sensor, a blood oxygen level sensor, and an impedance sensor, configured to monitor the physiological parameters of each user for determining the one or more physiological parameters; and the one or more neuromodulation devices selected from a group comprise at least one of: a transcutaneous electrical nerve stimulation (TENS) device, an electromyographic stimulation device, a spinal cord stimulation device, a dorsal root ganglion stimulation device, a peripheral nerve stimulation device, and a deep brain stimulation device.

3. The artificial intelligence (AI)-based system of claim 1, wherein the one or more physiological parameters sensing endpoint devices are selected from a group comprises at least one of: an accelerometer, a three-dimensional space measurement sensor, and a cutaneous sensor, configured to monitor the physiological parameters of each user for determining the one or more physiological parameters and transferred to the associated neuromodulation device.

4. The artificial intelligence (AI)-based system of claim 1, wherein the connectivity interface is selected from a group comprises at least one of: a system bus, Bluetooth, wireless fidelity (Wi-Fi), Zigbee, and proprietary wireless protocols to connect the one or more neuromodulation devices with the one or more physiological parameters sensing endpoint devices and the one or more server devices.

5. The artificial intelligence (AI)-based system of claim 1, wherein the one or more physiological parameters comprise at least one of: heart rate, muscle activity, skin conductivity, blood oxygen levels (SpO$_2$), blood pressure, temperature, respiratory rate, electrical impedance, nerve activity, and user posture and movement.

6. The artificial intelligence (AI)-based system of claim 1, wherein the user-centric data comprises at least one of: user operational parameter preferences, therapy goals, and user feedback on the induced electrical signals for the user-centric neuromodulation therapy preferences.

7. The artificial intelligence (AI)-based system of claim 1, wherein at least one of: the one or more artificial intelligence models and the one or more machine learning models comprises at least one of: supervised learning models, unsupervised learning models, reinforcement learning models, time series analysis models, and natural language processing (NLP) models, the supervised learning models comprise at least one of: neural networks, support vector machines (SVM), random forests, and gradient boosting machines, to classify the one or more physiological parameters based on historical treatment data to determine the one or more user-centric operational parameters;

the unsupervised learning models comprise at least one of: a K-means clustering, a hierarchical clustering analysis, and a principal component analysis (PCA), to identify patterns in the one or more physiological parameters for classifying the one or more physiological parameters;

the reinforcement learning models comprise at least one of: a Q-learning model and Policy gradient methods, to optimize the user-centric neuromodulation therapy preferences through the user feedback;

the time series analysis models comprise at least one of: Recurrent Neural Networks (RNNs), Long Short-Term Memory (LSTM) networks, and autoregressive integrated moving average (ARIMA) models, to analyze and predict trends in the one or more physiological parameters over time; and the natural language processing (NLP) models configured to process the user-centric data to determine at least one of the: user operational parameter preferences, therapy goals, and user feedback for determining the one or more user-centric operational parameters.

8. The artificial intelligence (AI)-based system of claim 1, wherein the one or more user-centric operational parameters comprise at least one of: a pulse width, a stimulation amplitude, a stimulation frequency, a stimulation intensity, and an impedance, associated with the induced electrical signals.

9. The artificial intelligence (AI)-based system of claim 1, further comprising a plurality of modules, wherein the plurality of modules comprises:

a community module configured to connect the one or more users receiving a neuromodulation therapy to a network of cohort users for sharing at least one of: experiences, progress, and feedback, fostering a collaborative environment through at least one of: comments, follows, likes, and group interactions;

a logging module configured to generate log data for each user of the one or more users based on the user-centric neuromodulation therapy preferences, wherein the log data comprises at least one of: a therapy duration, therapy timelines, and the one or more user-centric operational parameters;

a provider identification module configured to connect the one or more users with one or more healthcare providers based on one or more attributes comprise at least one of: location, proficiency in the neuromodulation therapy, and acquaintance with the one or more neuromodulation devices;

an educational resource providing module configured to provide one or more educational resources to at least one of: the one or more users and the one or more healthcare providers, wherein the one or more educational resources comprise at least one of: instructional videos, neuromodulation therapy documentations, and one or more manuals related to at least one of: the neuromodulation therapy and the one or more neuromodulation devices;

a neuromodulation products recommendation module configured to depict at least one of: one or more advertisements and sponsored content on the one or more communication devices associated with each user of one or more users, for providing product suggestions related to the neuromodulation therapy; and a dashboard module operatively connected to the one or more communication devices, configured to display visual representations related to at least one of: neuromodulation therapy outcomes, real-time one or more physiological parameters, one or more user-centric operational parameters, and invoice data, for providing information to at least one of: the one or more users and the one or more healthcare providers regarding the neuromodulation therapy.

10. An artificial intelligence (AI)-based method for controlling operations of one or more neuromodulation devices based on one or more physiological parameters of one or more users, comprising:

determining, by one or more physiological parameters sensing endpoint devices, the one or more physiological parameters of each user of the one or more users;

transferring, by a connectivity interface, the determined one or more physiological parameters to an associated neuromodulation device of the one or more neuromodulation devices from the one or more physiological parameters sensing endpoint devices;

obtaining, by one or more server devices through a data-obtaining subsystem, at least one of: the one or more physiological parameters from the one or more neuromodulation devices and user-centric data from one or more communication devices associated with each user of one or more users;

processing, by the one or more server devices through a data-processing subsystem, the obtained at least one of: the one or more physiological parameters and the user-centric data using at least one of: one or more artificial intelligence models and one or more machine learning models for deciphering at least one of: multi-faceted patterns, correlations, and trends within at least one of: the one or more physiological parameters and the user-centric data;

generating, by the one or more server devices through an operational parameter generation subsystem, one or more user-centric operational parameters in each neuromodulation device of the one or more neuromodulation devices using at least one of: the one or more artificial intelligence models and the one or more machine learning models, based on the processed at least one of: the one or more physiological parameters and the user-centric data, for optimizing user-centric neuromodulation therapy preferences;

transmitting, by the one or more server devices through a data recommendation subsystem, the generated one or more user-centric operational parameters to the associated neuromodulation device of the one or more neuromodulation devices for controlling operations of the one or more neuromodulation devices;

optimizing, by a learning module configured with an adaptive learning model, at least one of: the one or more artificial intelligence models and the one or more machine learning models based on analyzing real-time at least one of: the one or more physiological parameters and the user-centric data;

providing, by a survey module, a pre-defined set of queries to one or more users during at least one of: a pre-treatment phase and a post-treatment phase to obtain at least one of: visual analog score (VAS) results, patient global impression of change (PGIC) results, Patient-Reported Outcomes Measurement Information System (PROMIS) score, Oxygen Desaturation Index (ODI), clinical trial data, and real-world data, to continuously update and optimize at least one of: the one or more artificial intelligence models and the one or more machine learning models;

monitoring, by a remote therapy monitoring (RTM) module, the real-time efficacy of the neuromodulation therapy by analyzing the obtained user-centric data to generate the one or more user-centric operational parameters; and analyzing, by a remote patient monitoring (RPM) module, obtained at least one of: the one or more physiological parameters and the user-centric data in real-time to alter the one or more user-centric operational parameters in the associated neuromodulation device, wherein the controlling operations comprise inducing electrical signals through the associated neuromodulation device of the one or more neuromodulation devices, on defined treatment areas on a body of an associated user of the one or more users based on the one or more user-centric operational parameters.

11. The artificial intelligence (AI)-based method of claim 10, wherein inducing electrical signals comprises:

delivering, by one or more electrode pads of each neuromodulation device of the one or more neuromodulation devices, the electrical signals as neuromodulation waveforms with frequencies ranging between 0.000001 hertz (Hz) to 100,000 hertz (Hz), each neuromodulation device of the one or more neuromodulation devices comprises at least one of: an electrocardiogram (ECG) sensor, an electromyography (EMG) sensor, a skin conductivity sensor, a blood oxygen level sensor, and an impedance sensor, configured to monitor the physiological parameters of each user for determining the one or more physiological parameters, the one or more neuromodulation devices selected from a group comprise at least one of: a transcutaneous electrical nerve stimulation (TENS) device, an electromyographic stimulation device, a spinal cord stimulation device, a dorsal root ganglion stimulation device, a peripheral nerve stimulation device, and a deep brain stimulation device.

12. The artificial intelligence (AI)-based method of claim 10, wherein the one or more physiological parameters sensing endpoint devices are selected from a group comprises at least one of: an accelerometer, a three-dimensional space measurement sensor, and a cutaneous sensor, configured to monitor the physiological parameters of each user for determining the one or more physiological parameters and transferred to the associated neuromodulation device.

13. The artificial intelligence (AI)-based method of claim 10, wherein transferring the determined one or more physiological parameters comprises:

utilizing at least one of: a system bus, Bluetooth, wireless fidelity (Wi-Fi), Zigbee, and proprietary wireless protocols to connect the one or more neuromodulation devices with the one or more physiological parameters sensing endpoint devices and one or more server devices.

14. The artificial intelligence (AI)-based method of claim 10, wherein the one or more physiological parameters comprise at least one of: heart rate, muscle activity, skin conductivity, blood oxygen levels ($SpO_2$), blood pressure, temperature, respiratory rate, electrical impedance, nerve activity, and user posture and movement.

15. The artificial intelligence (AI)-based method of claim 10, wherein the user-centric data comprises at least one of: user operational parameter preferences, therapy goals, and user feedback on the induced electrical signals for the user-centric neuromodulation therapy preferences.

16. The artificial intelligence (AI)-based method of claim 10, wherein at least one of: the one or more artificial intelligence models and the one or more machine learning models comprises at least one of: supervised learning models, unsupervised learning models, reinforcement learning models, time series analysis models, and natural language processing (NLP) models.

17. The artificial intelligence (AI)-based method of claim 10, wherein the one or more user-centric operational parameters comprise at least one of: a pulse width, a stimulation amplitude, a stimulation frequency, a stimulation intensity, and an impedance, associated with the induced electrical signals.

18. The artificial intelligence (AI)-based method of claim 10, further comprising:

connecting, by a community module, the one or more users receiving a neuromodulation therapy to a network of cohort users for sharing at least one of: experiences, progress, and feedback, fostering a collaborative environment through at least one of: comments, follows, likes, and group interactions;

generating, by a logging module, log data for each user of the one or more users based on the user-centric neuromodulation therapy preferences, wherein the log data comprises at least one of: a therapy duration, therapy timelines, and the one or more user-centric operational parameters;

connecting, by a provider identification module, the one or more users with one or more healthcare providers based on one or more attributes comprise at least one of: location, proficiency in the neuromodulation therapy, and acquaintance with the one or more neuromodulation devices;

providing, by an educational resource providing module, one or more educational resources to at least one of: the one or more users and the one or more healthcare providers, wherein the one or more educational resources comprise at least one of: instructional videos, neuromodulation therapy documentations, and one or more manuals related to at least one of: the neuromodulation therapy and the one or more neuromodulation devices;

depicting, by a neuromodulation products recommendation module, at least one of: one or more advertisements and sponsored content to the one or more communication devices associated with each user of one or more users, to provide product suggestions related to neuromodulation therapy; and displaying, by a dashboard module, visual representations related to at least one of: neuromodulation therapy outcomes, real-time one or more physiological parameters, one or more user-centric operational parameters, and invoice data, to provide information to at least one of: the one or more users and the one or more healthcare providers regarding the neuromodulation therapy.

19. A non-transitory computer-readable storage medium storing computer-executable instructions that, when executed by one or more servers, cause the one or more servers to perform one or more actions for controlling operations of one or more neuromodulation devices based on one or more physiological parameters of one or more users, the one or more actions comprising:

determining the one or more physiological parameters of each user of the one or more users;

transferring the determined one or more physiological parameters to an associated neuromodulation device of the one or more neuromodulation devices from the one or more physiological parameters sensing endpoint devices;

obtaining at least one of: the one or more physiological parameters from the one or more neuromodulation devices and user-centric data from one or more communication devices associated with each user of one or more users;

processing the obtained at least one of: the one or more physiological parameters and the user-centric data using at least one of: one or more artificial intelligence models and one or more machine learning models for deciphering at least one of: multifaceted patterns, correlations, and trends within at least one of: the one or more physiological parameters and the user-centric data;

generating one or more user-centric operational parameters in each neuromodulation device of the one or more neuromodulation devices using at least one of: the one or more artificial intelligence models and the one or more machine learning models, based on the processed at least one of: the one or more physiological parameters and the user-centric data, for optimizing user-centric neuromodulation therapy preferences; and transmitting the generated one or more user-centric operational parameters to the associated neuromodulation device of the one or more neuromodulation devices for controlling operations of the one or more neuromodulation devices;

optimizing with an adaptive learning model, at least one of: the one or more artificial intelligence models and the one or more machine learning models based on analyzing real-time at least one of: the one or more physiological parameters and the user-centric data;

providing a pre-defined set of queries to one or more users during at least one of: a pre-treatment phase and a post-treatment phase to obtain at least one of: visual analog score (VAS) results, patient global impression of change (PGIC) results, Patient-Reported Outcomes Measurement Information System (PROMIS) score, Oxygen Desaturation Index (ODI), clinical trial data, and real-world data, to continuously update and optimize at least one of: the one or more artificial intelligence models and the one or more machine learning models;

monitoring the real-time efficacy of the neuromodulation therapy by analyzing the obtained user-centric data to generate the one or more user-centric operational parameters; and analyzing obtained at least one of: the one or more physiological parameters and the user-centric data in real-time to alter the one or more user-centric operational parameters in the associated neuromodulation device, wherein the controlling operations comprise inducing electrical signals through the associated neuromodulation device of the one or more neuromodulation devices, on defined treatment areas on a body of an associated user of the one or more users based on the one or more user-centric operational parameters.

20. The non-transitory computer-readable storage medium of claim 19, wherein at least one of: the one or more artificial intelligence models and the one or more machine learning models comprises at least one of: supervised learning models, unsupervised learning models, reinforcement learning models, time series analysis models, and natural language processing (NLP) models.

* * * * *